US009433490B2

(12) United States Patent
McFetridge

(10) Patent No.: US 9,433,490 B2
(45) Date of Patent: Sep. 6, 2016

(54) MULTILAYERED IMPLANT MATERIALS DERIVED FROM AMNIOTIC MEMBRANE, METHODS OF MAKING THE MULTILAYERED IMPLANT MATERIALS, AND METHOD OF USING MULTILAYERED IMPLANT MATERIALS

(75) Inventor: Peter McFetridge, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 338 days.

(21) Appl. No.: 13/994,915

(22) PCT Filed: Dec. 22, 2011

(86) PCT No.: PCT/US2011/066786
§ 371 (c)(1),
(2), (4) Date: Jul. 17, 2013

(87) PCT Pub. No.: WO2012/088396
PCT Pub. Date: Jun. 28, 2012

(65) Prior Publication Data
US 2013/0289715 A1 Oct. 31, 2013

Related U.S. Application Data

(60) Provisional application No. 61/425,899, filed on Dec. 22, 2010.

(51) Int. Cl.
A61F 2/02 (2006.01)
A61F 2/06 (2013.01)
(Continued)

(52) U.S. Cl.
CPC .............. *A61F 2/02* (2013.01); *A61L 27/3604* (2013.01); *A61L 27/3804* (2013.01)

(58) Field of Classification Search
CPC .............. A61F 2/02; A61F 2/08; A61F 2/82; A61K 9/00; A61K 35/12; A61L 27/507
USPC ........................................ 623/1.41; 424/484
See application file for complete search history.

(56) References Cited

U.S. PATENT DOCUMENTS 7,622,299 B2    11/2009  Sanders et al.
2003/0187515 A1 10/2003  Hariri et al.
2007/0061015 A1  3/2007  Jensen et al.
(Continued)

FOREIGN PATENT DOCUMENTS

WO    8907425 A2    8/1989
WO    2006002128 A1  1/2006
(Continued)

OTHER PUBLICATIONS

The International Preliminary Report on Patentability dated Jul. 4, 2013.
(Continued)

*Primary Examiner* — Suzette J Gherbi
(74) *Attorney, Agent, or Firm* — Thomas Horstemeyer, LLP

(57) ABSTRACT

Exemplary embodiments of the present disclosure provide for multi-layered implantation materials, methods of making a multi-layered implantation material, methods of forming a multi-layered implantation material, methods of forming a multi-layered implantation material having a spiral roll cross-section, and the like.

30 Claims, 17 Drawing Sheets

(51) Int. Cl.
*A61L 27/36* (2006.01)
*A61L 27/38* (2006.01)

(56) References Cited

U.S. PATENT DOCUMENTS

| | | | |
|---|---|---|---|
| 2007/0293937 A1* | 12/2007 | Biggs | A61L 27/34 623/1.13 |
| 2008/0069895 A1 | 3/2008 | Liu et al. | |
| 2008/0215087 A1* | 9/2008 | Pavcnik | A61B 17/12022 606/213 |
| 2008/0248079 A1 | 10/2008 | Dempsey et al. | |
| 2009/0175954 A1 | 7/2009 | Kinoshita et al. | |
| 2010/0010453 A1 | 1/2010 | Riemelmoser | |
| 2010/0058952 A1 | 3/2010 | Yang et al. | |
| 2010/0124569 A1* | 5/2010 | Abbot | A61K 35/50 424/484 |
| 2010/0228335 A1* | 9/2010 | Schorgl | A61L 31/005 623/1.15 |
| 2010/0239556 A1* | 9/2010 | Rayner | A61K 38/44 424/94.4 |
| 2013/0289715 A1* | 10/2013 | McFetridge | A61L 27/3604 623/1.41 |
| 2014/0148839 A1* | 5/2014 | Pavcnik | A61B 17/12131 606/191 |
| 2015/0010609 A1* | 1/2015 | Tom | A61K 35/50 424/423 |

FOREIGN PATENT DOCUMENTS

| | | |
|---|---|---|
| WO | 2006090696 A1 | 8/2006 |
| WO | 2007010305 A2 | 1/2007 |
| WO | 2008102847 A1 | 8/2008 |
| WO | 2009044408 A1 | 4/2009 |

OTHER PUBLICATIONS

The International Search Report and Written Opinion dated Sep. 27, 2012.

* cited by examiner

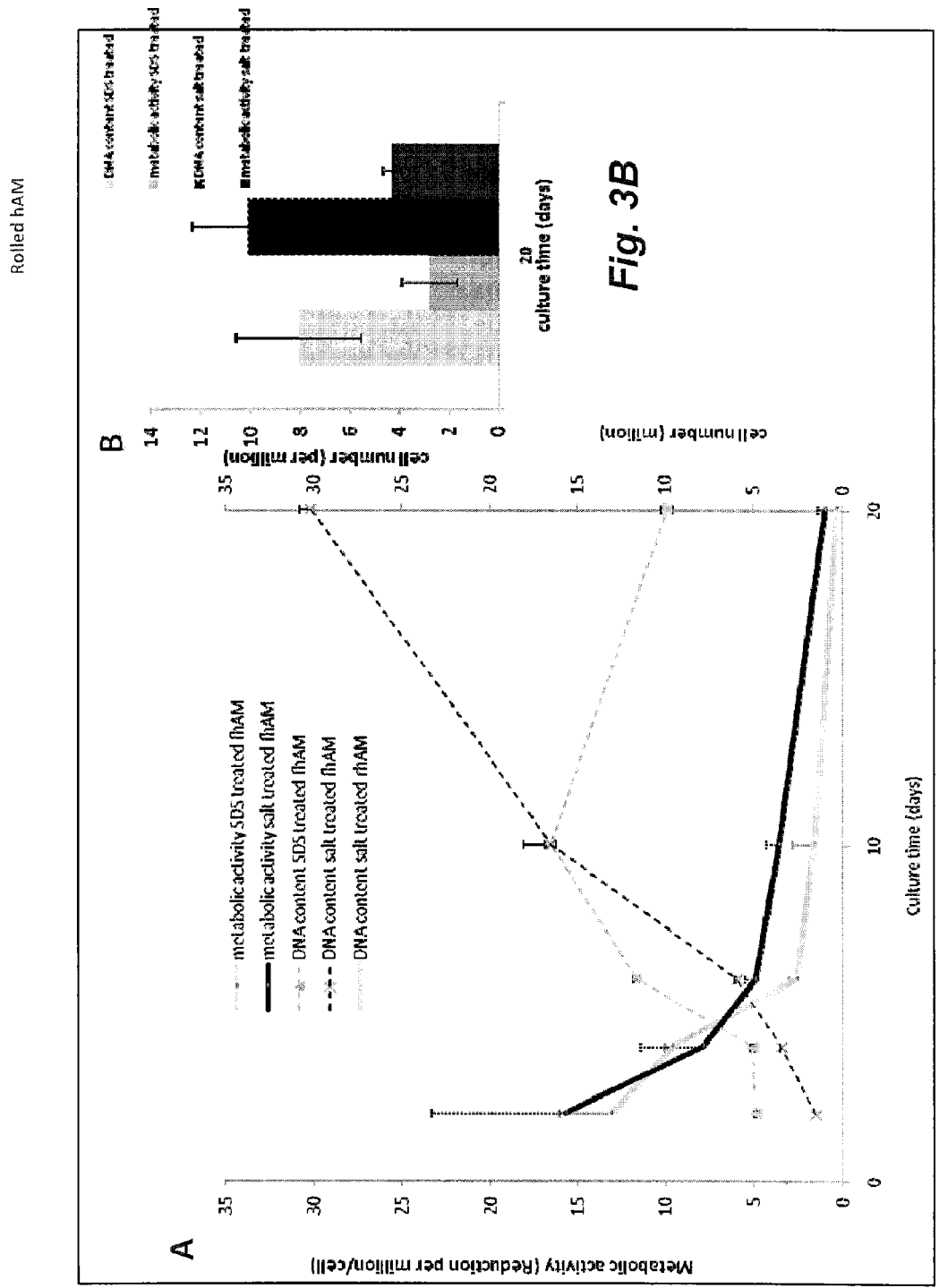

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cggagcacgg agacgggtat                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgaaggggaa gacgcacagc                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gtatttgatg gcatcgctca                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cattccctgc aaagaacaca                                               20

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ctcgctggac gttggaggaa agaa                                          24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
tgaaccacag gtaccagatg ggct                                          24

<210> SEQ ID NO 7
<211> LENGTH: 21
<212> TYPE: DNA
<213> ORGANISM: Artificial Sequence

```
<220> FEATURE:
<223> OTHER INFORMATION: forward primer

<400> SEQUENCE: 7
tcagcaacga gctggccaca g                                              21

<210> SEQ ID NO 8
<211> LENGTH: 22
<212> TYPE: DNA
<213> ORGANISM: Artificial Sequence
<220> FEATURE:
<223> OTHER INFORMATION: reverse primer

<400> SEQUENCE: 8
tggcgttgat gcgctgggac tc                                             22

<210> SEQ ID NO 9
<211> LENGTH: 18
<212> TYPE: DNA
<213> ORGANISM: Artificial Sequence
<220> FEATURE:
<223> OTHER INFORMATION: reverse primer

<400> SEQUENCE: 9
ggtgggatgc tcttcagg                                                  18

<210> SEQ ID NO 10
<211> LENGTH: 18
<212> TYPE: DNA
<213> ORGANISM: Artificial Sequence
<220> FEATURE:
<223> OTHER INFORMATION: forward primer

<400> SEQUENCE: 10
catcaccaac tgggacga                                                  18

<210> SEQ ID NO 11
<211> LENGTH: 24
<212> TYPE: DNA
<213> ORGANISM: Artificial Sequence
<220> FEATURE:
<223> OTHER INFORMATION: reverse primer

<400> SEQUENCE: 11
tcttgcagtg gtaggtgatg ttct                                           24

<210> SEQ ID NO 12
<211> LENGTH: 19
<212> TYPE: DNA
<213> ORGANISM: Artificial Sequence
<220> FEATURE:
<223> OTHER INFORMATION: forward primer

<400> SEQUENCE: 12
atgtggccat ccagctgac                                                 19
```

MULTILAYERED IMPLANT MATERIALS DERIVED FROM AMNIOTIC MEMBRANE, METHODS OF MAKING THE MULTILAYERED IMPLANT MATERIALS, AND METHOD OF USING MULTILAYERED IMPLANT MATERIALS

CROSS-REFERENCE TO RELATED APPLICATION(S)

This application is the 35 U.S.C. §371 national stage of PCT application PCT/US2011/066786, filed Dec. 22, 2011 which claims priority to and the benefit of U.S. Provisional Application Ser. No. 61/425,899, filed Dec. 22, 2010, both of which is are hereby incorporated by reference herein in their entirety.

STATEMENT REGARDING FEDERALLY SPONSORED RESEARCH OR DEVELOPMENT

This invention was made with government support under NIH Grant No. R01 1050916 awarded by the U.S. National Institutes of Health of the United States government. The government has certain rights in the invention.

BACKGROUND

In the search for biomaterials that improve tissue engineered implant function and viability, a number of alternate strategies have been investigated. From a materials perspective, two diametrically opposite approaches have been taken, with one group developing new (or modifying existing) synthetic polymers (Puskas & Chen (2004) *Biomacromolecules* 5: 1141-1154; Madigan et al., (2009) *Respir. Physiol. Neurobiol.* 169: 183-199; Gunatillake et al., (2006) *Biotechnol. Annu. Rev.* 12: 301-347), and the other using biologically derived materials either as purified compounds or directly as processed ex vivo tissues (Dutta & Dutta (2009) *Biotechnol. Adv.* 27: 334-349). The use of ex vivo-derived biomaterials range from whole hearts and kidneys (Rastogi & Nissenson (2009) *Clin. J. Am. Soc. Nephroi.* 4: S132-136; Dohmen & Konertz (2009) *Ann. Thorac. Cardiovasc. Surg.* 15: 362-367) to skin and blood vessels (Ravi & Chaikof (2010) *Regen. Med.* 5: 107-120; Shevchenko et al., (2010) *J. R. Soc. Interface.* 7: 229-258). Small diameter blood vessel grafts are extremely sensitive to failure from thrombosis or inflammatory responses, and, as such, materials that may minimize, or promote a more quiescent phenotype once implanted may prove more successful.

SUMMARY

Exemplary embodiments of the present disclosure provide for multi-layered implantation materials, methods of making multi-layered implantation materials, methods of forming a multi-layered implantation material, methods of forming a multi-layered implantation material having a spiral roll cross-section, and the like.

An exemplary embodiment of a multi-layered implantation material, among others, includes a multi-layered amniotic membrane and a population of cells disposed on said membrane layers. In an embodiment, the multi-layered implantation material has a spiral roll cross-section having an inner edge, an outer edge, and a longitudinal axis along the length of the multi-layered implantation material and can have a lumen along the longitudinal axis. In an embodiment, the population of cells can include: a stem cell, an endothelial cell, a smooth muscle cell, a fibroblast, and a combination thereof. In embodiments, the population of cells is a homogeneous population. In other embodiments, the population of cells can be a heterogeneous population of cells. In an embodiment, the multi-layered implantation material is an implant for a subject human or animal, more specifically is an implant in a duct of a subject human or animal or an implant in a ureter or a vascular vessel of a subject human or animal. In an embodiment, the multi-layered amniotic membrane has a plurality of holes drilled therein. In an embodiment, the multi-layered amniotic membrane is cross-linked with a cross-linking agent.

An exemplary embodiment of forming a multi-layered implantation material, among others, includes: obtaining an amniotic membrane; culturing the amniotic membrane under conditions whereby the membrane is colonized by a population of cells; and forming a multilayered implantation material including alternate layers of the amniotic membrane and the population of cells disposed on the amniotic membrane. In an embodiment, the method includes decellularizing the amniotic membrane to produce a decellularized amniotic membrane. In an embodiment, the method includes drilling a plurality of holes in the amniotic membrane. In an embodiment, the method includes freeze drying the multilayered implantation material. In an embodiment, the method includes cross-linking the multi-layered amniotic membrane using a cross linking agent.

An exemplary embodiment of forming a multi-layered implantation material having a spiral roll cross-section, among others, includes: wrapping a multi-layered implantation material around itself to form a multi-layered structure having the spiral roll cross-section, wherein the multi-layered implant has two or more spiral layers. In an embodiment, the method includes freeze drying the multi-layered structure. In an embodiment, the method includes cross-linking the multi-layered structure using a cross linking agent. In an embodiment, the method includes drilling a plurality of holes in the multi-layered structure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 3A and 3B are a pair of graphs illustrating a comparison of SMCs metabolic activity and cell density between SDS and salt decellularized flat (FIG. 3A) and rolled (FIG. 3B) hAM. In FIG. 3A, straight lines represent the percentage of Alamar Blue reduction per million/cells and broken lines represent cell density (n=9). FIG. 3B illustrates rolled hAM DNA content and metabolic activity at day 20 of cell culture (n=3).

Figure 1:
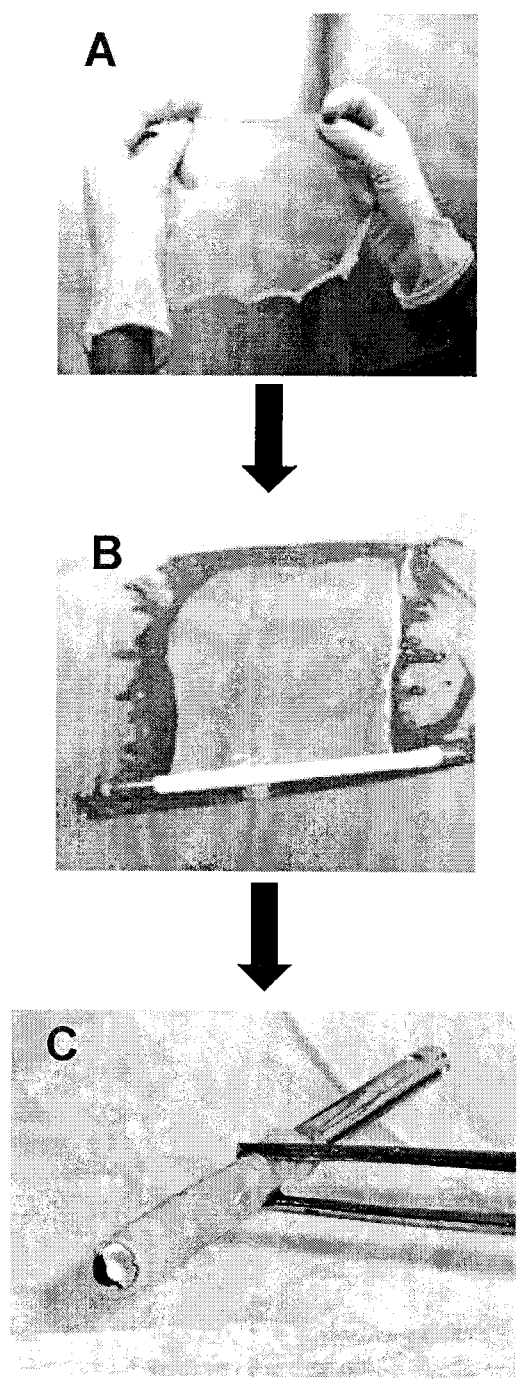
FIG. 1 is a series of digital images showing the hAM seeding and rolling procedure according to the disclosure. The human amniotic membrane was first decellularized (A), then under sterile conditions was cut in 12.4×8.4 cm² rectangular shape and seeded with SMCs in a concentration of 6×10⁴ cells/cm² (B). After 20 days of cell culture, the hAM have been tightly rolled and stuck to a glass mandrel (C).

The drawings are described in greater detail in the description and examples below.

The details of some exemplary embodiments of the structures, methods and the like of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Discussion

Exemplary embodiments of the present disclosure provide for multi-layered implantation materials and implants, methods of making multi-layered implantation materials and implants, methods of forming a multi-layered implantation material or an implant (e.g., for a subject human or animal), methods of forming a multi-layered implantation material or an implant having a spiral roll cross-section, and the like.

Many similarities exist between the clinically used porcine intestinal submucosa (SIS) for vascular constructs (Robotin-Johnson et al., (1998) *J. Thorac. Cardiovasc. Surg.* 116: 805-811) and the human amniotic membrane (hAM) morphology and function (Fan et al., (2006) *Zhongguo Xiu Fu Chong Jian Wai Ke Za Zhi* 20: 155-160). The small intestinal submucosa (SIS) and the hAM, are both composed predominantly of collagen type 1, have similar thicknesses (up to 100 um), and function as barrier membranes. The hAM has been used as a scaffold for ocular, skin, cartilage and peripheral nerve regeneration with promising results due to its unique structure and composition (Gris et al., (1999) *Ann. Transplant.* 4: 82-84; Kheirkhah et al., (2008) *Arch. Ophthalmol.* 126: 1059-1066; Maharajan et al., (2007) *Clin. Experiment. Ophthalmol.* 35: 140-147; Meller et al., (2000) *Ophthalmology* 107: 980-989; Tamhane et al., (2005) *Ophthalmology* 112: 1963-1969; Jin et al., (2007) *Tissue Eng.* 13: 693-702; Mligiliche et al., (2002) *J. Biomed Mater. Res* 63: 591-600; Mohammad et al., (2000) *Plast. Reconstr. Surg.* 105: 660-666). Although the hAM has not been used as a scaffold for blood vessel regeneration, previous investigations have shown the membrane to provide an excellent environment for cell growth and differentiation that may transfer to the vascular environment (Niknejad et al., (2008) *Eur. Cell. Mater.* 15: 88-99; Lekhanont et al., (2009) *Mol. Vis.* 15: 1294-1302; Yu et al., (2009) *Cell Transplant.* 18: 111-118; Shortt et al., (2009) *Biomaterials* 30: 1056-1065).

hAM has presented a number of desirable characteristics, including being a biocompatibile and biostabile material as well as having non-inflammatory, non-toxic, non-carcinogenic, non-immunogenic properties (Niknejad et al., (2008) *Eur. Cell Mater.* 15: 88-99). Additionally, hAM is vasoactive (Mohammad et al., (2000) *Plast. Reconstr. Surg.* 105: 660-666); thromboresistant (Liliensiek et al., (2009) *Tissue Eng. PartA* 15: 2643-2651; Hao et al., (2000) *Cornea* 19: 348-352); able to remodel (Mohammad et al., (2000) *Plast. Reconstr. Surg.* 105: 660-666; Liliensiek et al., (2009) *Tissue Eng. PartA* 15: 2643-2651; Dua et al., (1999) *Br. J. Ophthalmol.* 83: 748-752; Faulk et al., (1980) *Lancet* 1: 1156-1158); infection resistant (Gajiwala & Lobo (2003) *Cell Tissue Bank* 4: 141-146); suture resistant (Szurman et al., (2006) *Cornea* 25: 460-466); and readily available in appropriate situations. As discussed by Campbell and Campbell ((2007) *Curr. Pharm. Biotechnol.* 8: 43-50) all these characteristics are highly advantageous for blood vessel construction.

One of the primary challenges in vessel engineering is the choice of an appropriate scaffold allowing the new formed tissue to respond and withstand mechanical and biological stimuli from the implant site in the host body. The human amniotic membrane (hAM) is an abundant birthing tissue that, due to its unique structure, composition, and neonatal derivation, has been used in a number of applications as an ex vivo-derived scaffold for tissue repair. The hAM has shown promising results in a number of diverse applications such as ocular, skin, cartilage and peripheral nerve regeneration (Gris et al., (1999) *Ann. Transplant.* 4: 82-84; Kheirkhah et al., (2008) *Arch. Ophthalmol.* 126: 1059-1066; Maharajan et al., (2007) *Clin. Experiment. Ophthalmol.* 35: 140-147; Meller et al., (2000) *Ophthalmology* 107: 980-989; Tamhane et al., (2005) *Ophthalmology* 112: 1963-1969; Jin et al., (2007) *Tissue Eng.* 13: 693-702; Mligiliche et al., (2002) *J. Biomed Mater. Res* 63: 591-600; Mohammad et al., (2000) *Plast. Reconstr. Surg.* 105: 660-666).

As an alternative approach to synthetic materials, an exemplary embodiment of the present disclosure includes the modification of the rich extracellular matrix of the hAM to form a multi-layered implantation material (e.g., a multi-layered, cell dense, tubular scaffold (e.g., having a spiral roll cross-section)), which, in an embodiment, can be used to regenerate blood vessels. In an embodiment, the processed hAM was evaluated as a single membrane and as a tubular, rolled multilayered structure for its ability to support seeded human smooth muscle cell function. The phrase "multi-layered implantation material" can also be referred to a "multi-layered implantation tubular scaffold", a "multi-layered material", or the like, and when having desired dimensions for implantation, these can be referred to as "a multi-layered implant".

In an embodiment, the hAM was used to generate a multi-layered scaffold (tubular or flat) from a flat single layered sheet of the membrane. In an embodiment, the amniotic membrane is used a direct implant or is processed to stabilise the material against degradation, by a variety of methods to decellularize or cross-link. In particular, the multi-layer, tubular scaffold can be used to engineer de novo blood vessels. The "layer by layer" approach of the present constructs of the present disclosure provides a novel approach to manufacture the hAM in vitro into different sizes and diameters, allowing the possibility to use this material in a range of different applications.

Figure 16:
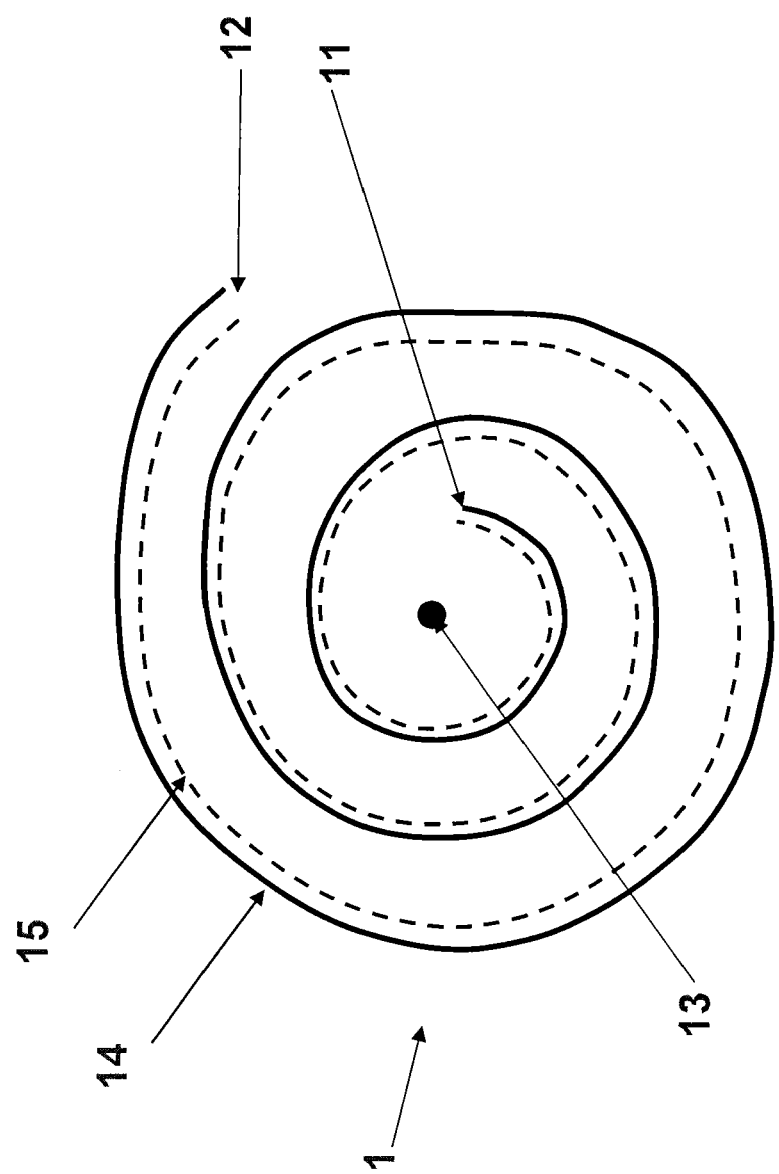
FIG. 16 illustrates a transverse section of a spiral roll embodiment of a multilayered implant according to the disclosure.
Figure 17A:
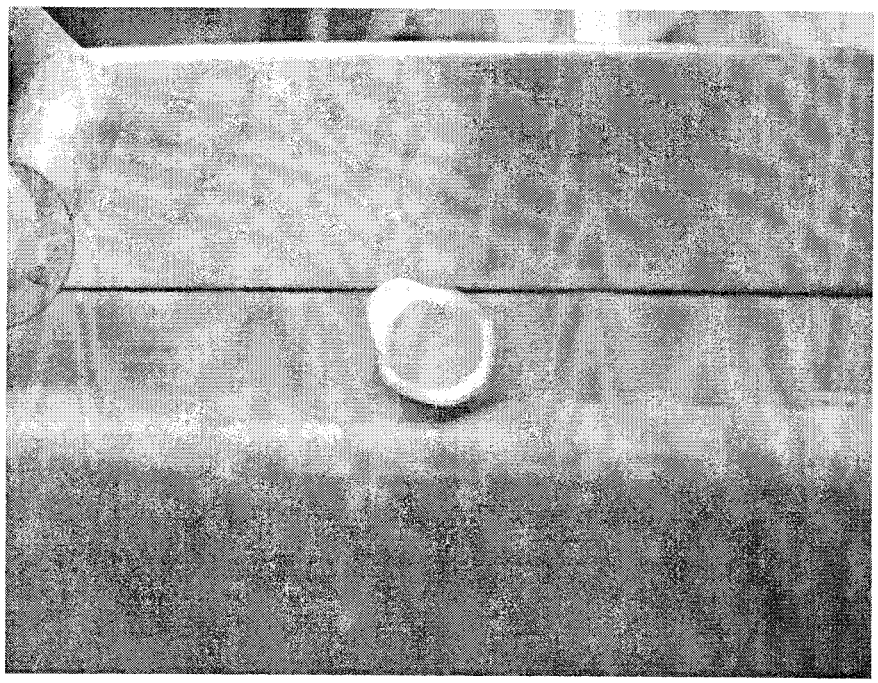
FIGS. 17A and 17B illustrates images of a freeze dried scaffold for blood vessel.
Figure 17B:
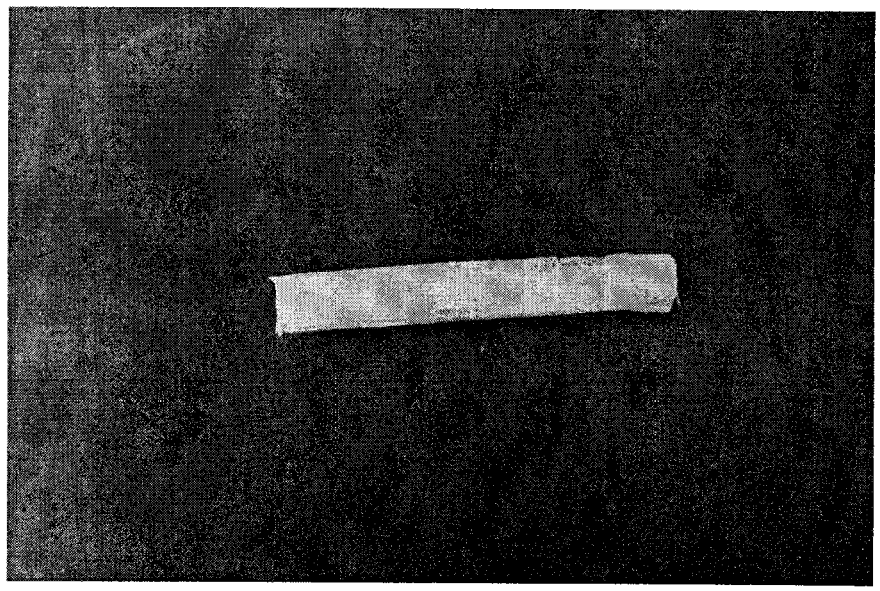

One embodiment of the present disclosure is illustrated in FIG. 16. In this transverse view, a multi-layered implantation tubular scaffold 1 of the disclosure has an inner edge 11, an outer edge 12, and a longitudinal axis 13 along the length of the multi-layered implantation tubular scaffold 1. FIG. 16 also illustrates the alternate layers of an amniotic membrane 14 (e.g., decellularized hAM or non-decellularized hAM) and a population of cells 15 (e.g., one or more cell types) disposed on the membrane layers 14. In embodiments, the population of cells can be on one or both sides of the amniotic membrane, multiple layers of cells can be on the same side of the amniotic membrane, and combinations thereof.

As shown in FIG. 16, the rolled embodiment of the multi-layered implantation tubular scaffold begins at the inner edge 11 and spirals outwards to the outer edge 12. The multi-layered implantation tubular scaffold 1 can include two or more spiral layers (e.g., overlap of a layer of a membrane layer with an adjacent layer of a membrane). The number of layers can depend upon the use of the multi-layered implantation tubular scaffold 1, the amount of multi-layered implantation material, the type(s) of cells in the population of cells 15, and the like. In an embodiment, the multi-layered implantation tubular scaffold can be made of one or more portions of a flat sheet membrane, where each separate portion is wrapped around the proceeding portion forming the multi-layered implantation tubular scaffold.

In an embodiment, the membrane layer 14 can have a thickness of about 45 µm as a single layer to about 1000 µm, as multiple layers ranging from 2 to 40 layers. The length and width of the membrane layer 14 and the population of cells 15 can vary depending upon the desired dimensions (e.g., mm's to cm's or more), use, and/or purpose. In an embodiment, the multi-layered implantation tubular scaffold 1 can have an outside diameter of about 1 mm to 30 mm. In an embodiment, the multi-layered implantation material can have a width along the longitudinal axis of about 0.01 mm to 1200 mm. In an embodiment, two or more multi-layered implantation materials aligned side-by-side along the longitudinal axis can be used to make a long structure that can be used in a graft in a peripheral bypass.

As shown, the multi-layered implantation tubular scaffold 1 has a lumen. In general, the lumen has a circular cross-section, but other embodiments can have a substantially circular cross-section (e.g., oval). In an embodiment, the lumen can have a diameter of about 0.2 mm to 30 mm.

In an embodiment, the multi-layered implantation tubular scaffold can have a spiral cross-section (See FIG. 16). The spiral cross-section shown in FIG. 16 does not include a lumen, but other embodiments of the spiral cross-section can have a lumen oriented along the length of the longitudinal axis of the spiral roll, and the multi-layered implantation tubular scaffold has a spiral cross-section around the lumen. In an embodiment, the spiral cross-section having a lumen can be formed by wrapping the multi-layered implantation tubular scaffold around a structure such as a tube or rod so that a specific diameter of the lumen can be formed. It is also contemplated that the cross-section of the lumen can be polygonal (e.g., square, rectangular, triangle, hexagon, and the like), where the multi-layered implantation tubular scaffold is wrapped around a structure having the desired cross-section.

In an embodiment, the amniotic membrane can include a plurality of holes. In an embodiment, the holes are made through the amniotic membrane, and in another embodiment, the holes are not through the entire thickness of the amniotic membrane. In an embodiment, the holes can be formed prior to processing the material or at one or more times during the processing of the material, and/or after the material is processed. In an embodiment, the holes can be formed using a laser drilling technique, a manual drilling technique, or by direct puncture, or a combination thereof. In an embodiment, the holes can have a diameter of about 1 to 500 micrometers. In an embodiment, the holes in the amniotic membrane can have the same diameter or can have two or more diameters, where the different diameter holes can be randomly placed or can be placed in a pattern (e.g., to increase growth of the population of cells, increase vascularity, increase fluid communication between or among the layers, and the like). In an embodiment, one or more pairs of drilled holes are spaced apart by about 1 micrometer to 10 millimeters, where the spacing can be consistent or in a pattern or the holes can be randomly spaced.

In an embodiment, the holes are positioned so that when the amniotic membrane is formed into a multi-layered implantation tubular scaffold, the holes are not aligned. In another embodiment, a portion of the holes are positioned so that when the amniotic membrane is formed into a multi-layered implantation tubular scaffold, the holes are aligned. In an embodiment, the holes are positioned randomly so that when the amniotic membrane is formed into a multi-layered implantation tubular scaffold, the alignment of the holes is random.

In an embodiment, the layers of the multi-layered implantation tubular scaffold can be cross-linked (e.g., bonded) to one another. In an embodiment, the cross-linking can be accomplished using a cross-linking agent such as, but not limited to: glutaraldehyde, methylene blue, a formaldehyde, a carbodiimide, formaldehyde, ethanol, or other alcohols, and a combination thereof. An example of a crosslinking agent is glutaraldehyde and can have a concentration of about 0.1 to 10% for <1 minute to days (or weeks). Concentrations for other cross-linking agents can be selected as needed to accomplish the desired amount of cross-linking.

As mentioned above, the amniotic membrane can be decellularized or non-decellularized. Thus, in each of the embodiments described herein, the amniotic membrane can be decellularized or non-decellularized. In an embodiment, where two or more different amniotic membranes are used, each membrane can be decellularized or non-deceliularized, or one or more layers can be decellularized, while others are non-decellularized. It should be noted that in some instances, the discussion may be directed to just one of decellularized or non-decellularized amniotic membrane, but it should be understood that the other of the two not mentioned can be processed or used in a similar manner unless specifically stated that this is not the case.

In an embodiment where the amniotic membrane is not decellularized, the amniotic membrane can include non-amniotic tissue such as neonatal cells, whole or partial components of the chorionic membrane, and a combination thereof. In an embodiment where the amniotic membrane is decellularized, the amniotic membrane is substantially free (e.g., the term substantially free means that the amniotic membrane has about 10% or less, about 5% or less, about 3% or less, about 2% or less, about 1% or less, about 0.5% or less, about 0.1% or less) of non-amniotic tissue.

As mentioned above, embodiments of the present disclosure contemplate methods of making a multi-layered implantation tubular scaffold (or multi-layered implant or multi-layered implantation material). In an embodiment, the method can include: culturing the amniotic membrane under conditions whereby the membrane is colonized by a population of cells and forming a multilayered implantation material comprising alternate layers of the amniotic membrane and the population of cells disposed on the amniotic membrane. In addition, the method can include one or more of the following: decellularizing the amniotic membrane to produce a decellularized amniotic membrane; drilling a plurality of drilled holes in the amniotic membrane; freeze drying the multi-layered implantation tubular scaffold; cross-linking the multi-layered structure; or one or more combinations of these.

An embodiment of the method described in the following paragraphs focuses on a decellularized amniotic membrane, however, non-decellularized amniotic membrane can be processed in the same manner (e.g., cultured, wrapping, cross-linking, freeze drying, drilling, and one or more combinations thereof).

In an embodiment, the multi-layered implantation tubular scaffold can be formed by decellularizing the amniotic membrane to produce a decellularized amniotic membrane. In an embodiment, the decellularizing process can take about 2 minutes to several days depending on the specific chemistry being used. In an embodiment, the amniotic membrane can be decellularized using sodium dodecyl (e.g., about 0.03 to 2% % sodium dodecyl sulfate, where a larger concentration could be used if appropriate), NaCl (e.g., about 4M NaCl, where a larger concentration could be used if appropriate), peracetic acid (PAA) (e.g., about 0.1-1% PAA, where a larger concentration could be used if appropriate), Triton X-100 (e.g., about 0.1 to 5% where a larger concentration could be used if appropriate), or a variety of other surfactants, alcohols or other solubilizing agents, and a combination thereof.

In particular, the effect of different decellularization methods on cell function throughout the tissue remodelling phase was assessed. Smooth muscle cell behavior on hAM sections decellularized with about 0.03% (e.g., 0.01 to 5%) sodium dodecyl sulfate and about 4M NaCl (e.g., 0.1 to 10 M) was assessed to determine variation in cell adhesion, cell density, metabolic activity, changes in the materials biomechanical properties, and gene expression over 40 days of static cell culture. In an embodiment, the hAM was prepared using two different decellularization methods: sodium dodecyl sulfate (0.03%) and 4M NaCl, and the effects on cell adhesion, cell density, metabolic activity and changes in the material biomechanical properties were evaluated over a 40 days culture period. Results show that both SDS and salt decellularized flat constructs stimulated SMC growth and proliferation. The rolled hAM displayed significant differences in relative gene expression between the two decellularization approaches, where cells seeded on salt-treated hAM adopted a "synthetic" phenotype whereas SMCs seeded on SDS-treated hAM induced a more "contractile" profile.

In an embodiment, holes can be made into the amniotic membrane. Details regarding the holes, the patterns of holes, and the like, are descried herein. As mentioned above, the holes can be formed using a laser, manually, or a combination thereof. In an embodiment, the holes can be formed at one or more times during the method (e.g., before and/or after wrapping). In an embodiment, the holes can be formed in the amniotic membrane, prior to decellularization of the amniotic membrane, after decellularization of the amniotic membrane, before culturing, after culturing, before wrapping, after wrapping, before freeze drying, after freeze drying, before cross-linking, after cross-linking, and the like, and combinations thereof.

In an embodiment, forming the holes can be advantageous to increase porosity (e.g., improve nutrient transport to improve tissue regeneration relative to structures without the holes), provide paths for the formation of microvessels, improve transport condition of the material relative to not including the holes, improve capacity to seed cells relative to not including the holes, improve capacity to promote cellular infiltration by providing a pathway for cells to move more freely relative to not including the holes, encourage recellularization and/or vascularization, control mechanical compliance of the material, and combinations thereof.

In an embodiment, the decellularized amniotic membrane can be cultured under conditions whereby the membrane is colonized by a population of cells (e.g., one side of the decellularized amniotic membrane, on both sides of the decellularized amniotic membrane, multiple layers on the same side of the decellularized amniotic membrane, and combinations thereof). In an embodiment, the population of cells can be selected from smooth muscle cells, stem cells, endothelial cells, fibroblasts, neuronal, skeletal muscle (others too), and a combination thereof. In an embodiment, the population of cells is a homogeneous population of cells; in other embodiments it can be a heterogeneous population of cells. The term "conditions" means environment conditions that replicate in vivo conditions. This can be under traditional static culture (no dynamic movement) or conditioned in a bioreactor or similar device to mechanically condition cells.

Subsequently, a multi-layered implantation material is formed having a layer of the decellularized amniotic membrane and one or more layers of a population of cells (e.g., on both sides of the decellularized amniotic membrane, multiple layers on the same side of the decellularized amniotic membrane, and combinations thereof). In an alternative embodiment, the multi-layered implantation material can be formed and then cultured. In an embodiment, the multi-layered implantation material is a planar structure. In an embodiment, the multi-layered implantation material is a multi-layered implantation tubular scaffold. In an embodiment, a planar first multi-layered implantation material can be disposed on a second planar multi-layered implantation material to form a planar multi-layered implantation material.

In an embodiment, the multi-layered implantation tubular scaffold (e.g., a multi-layered implant having a spiral roll cross-section) can be formed by wrapping a multi-layered implantation material around itself to form a multi-layered structure having the spiral roll cross-section. In an embodiment, the multi-layered implantation material can be wrapped around to form two or more spiral layers. In an embodiment, a first multi-layered implantation material can be wrapped around to form the multi-layered implantation tubular scaffold and then a second multi-layered implantation material can be wrapped around the multi-layered implantation tubular scaffold made from the first multi-layered implantation material. More than two multi-layered implantation material structures can be wrapped together. In an embodiment, a planar first multi-layered implantation material can be disposed on a second planar multi-layered implantation material and then this structure can be wrapped in any way described herein. For each of these, the wrapping can include wrapping the multi-layered structure(s) around a structure to form a lumen. Thus, each of the embodiments described herein can be designed to have a lumen. As can be envisioned by the teachings of the present disclosure, there are multiple ways to combine one or more multi-layered implantation materials and/or wrap the one or more multi-layered implantation materials, and these are intended to be covered by the present disclosure.

In an embodiment, the multi-layered implantation tubular scaffold can be cross-linked (e.g., bonded to one another, for example by freeze drying the material around a mandrel of appropriate size (0.2 mm to 30 mm)) to one another. In an embodiment, the cross-linking can be accomplished using a cross-linking agent such as: glutaraldehyde, methylene blue, a formaldehyde, a carbodiimide, or by freeze drying (e.g., freeze drying partially cross-links the material), or a combination thereof. In an embodiment, the multi-layered implantation tubular scaffold is exposed to the cross-linking agent for about 2 hours in about a 5% concentration. In an embodiment, the multi-layered implantation tubular scaffold can be freeze dried.

In an embodiment, the freeze drying process can include freezing the multi-layered implantation tubular scaffold to about 0 to $-30°$ C. or about $-20°$ C. and holding at that temperature for about 2 to 24 hours (or more) or about 12 hours. The frozen multi-layered implantation tubular scaffold can then undergo freeze-drying in a Millrock Bench-Top Freeze-Drier (Millrock Technologies Kingston, N.J.) or similar freeze-drier at about $-89°$ C. ($+/-10°$ C.), at about 4 and 8 mT, for about 6 to 18 hours or about 12 hours.

In an embodiment, once the multi-layered implantation tubular scaffold is freeze dried, it can be thawed out by placing in suitable refrigerator, such as a 5° C. refrigerator, for a suitable time frame (e.g., about 1 hour or longer). In another embodiment, the samples can also be thawed by using specific (controlled) temperature gradient devices to thaw (e.g., at a rate of 1° C. per minute) the sample. Once the sample is thawed to about room temperature, the sample can be used directly.

In an embodiment, the multi-layered implantation material can be implanted in a subject human or animal, in a duct of a subject human or animal, or in a ureter or a vascular vessel of a subject human or animal. In an embodiment, the multi-layered implantation material can be used as a thick tissue patch for an ulcer, burns, and the like. In this embodiment, the multi-layered implantation material may be planar (e.g., includes one or more layers of separate multi-layered implantation material) as opposed to being wrapped around itself.

In an embodiment, the multi-layered implantation material can be cut to appropriate dimensions for a particular application to form a multi-layered implant (e.g., a single multi-layered implantation material or two or more combined together). Thus, the dimensions of the multi-layered implant can be controlled during the preparation of the multi-layered implantation material (e.g., diameter of the lumen, thickness of the layers, and the like) and then the length or depth of the multi-layered implant can be tailored for the specific use. In addition, the mechanical compliance of the multi-layered implantation material can be controlled (e.g., control the diameter of the lumen; thickness of the layers; presence of holes, diameter of holes, number of holes, pattern of holes, and the like). Further, the biological properties can be controlled by use and/or selection of the type or types of cells. Thus, embodiments of the present disclosure can be designed to accommodate many uses.

Now having described embodiments of the present disclosure in general, additional details will be provided about specific embodiments.

Cardiovascular diseases are the primary cause of death in western countries, with 37% of patients suffering from myocardial infarctions dying within 12 months due to performance limitations of current vascular grafts. Synthetic vascular grafts have proven successful for large diameter blood vessel replacement, but small diameter vascular graft (inner diameters of less than about 6 mm) remains problematic.

hAM was assayed as a multilayer structure that resembles a natural artery. The development of the multilayered technique, rolling the hAM into a tubular construct with cells seeded on each layer within the scaffold, allows development of cell dense materials for surgical implantation. In the clinic, the hAM has been used predominantly as a multi-layered patch for ulcer (Murphy et al., (2003) *Expert Opin. Pharmacother.* 4: 369-84; Matthews et al., (1982) *Obstet. Gynecol. Annu.* 11: 31-58; Prabhasawat et al., (2001) *Br. J. Ophthalmol.* 85: 1455-1463; Dekaris et al., *Coll. Antropol.* 25: 23-28) with a limited number of studies focusing on nerve regeneration (Mligiliche et al., (2002) *J. Biomed. Mater. Res.* 63: 591-600; Mohammad, J., et al., (2000) *Plast. Reconstr. Surg.* 105: 660-666; Davis et al., (1987) *Science* 236: 1106-1109; Lopez Ferrando et al., Arch. Soc. Esp. Oftalmol. 79: 27-31). However, in these studies the scaffold was used as an acellular material, not taking advantage of the material capacity to be seeded as a layered construct to speed and enhance tissue regeneration. The multilayer approach is particularly useful in the vascular area due to the large range of diameters and thicknesses of conduits that can be produced.

As described in general above, the present disclosure encompasses decellularization methods to prepare the scaffold for either direct implantation or, as in the tissue engineering methodology, cell seeding. The goal of any decellularization protocol is to effectively remove immunogenic cellular material while maintaining the biological activity and mechanical integrity of the extracellular matrix. A wide range of methods has been described in the literature with several specific to hAM decellularization (Jin et al., (2007) *Tissue Eng.* 13: 693-702; Wilshaw, et al., (2006) *Tissue Eng.* 12: 2117-2129; Koizumi et al., (2007) *Graefes Arch. Clin. Exp. Ophthalmol.* 245: 123-134; Lim et al., (2009) *Mol. Vis.* 15: 1962-1970; Portmann-Lanz et al., (2007) *Placenta* 28: 6-13). SDS, a commonly used ionic detergent, has been widely and effectively used as a decellularization agent with the hAM, however several studies have reported that ionic detergents tend to denature proteins by disrupting protein-protein interactions (Berglund et al., (2004) *Tissue Eng.* 10: 1526-1535).

Another decellularization method shown to be effective for cellular removal (Kim et al., (2002) *Int. J. Artif. Organs* 25: 791-797) is based on the use of concentrated sodium chloride, chemical treatment to disrupt nuclear acids and solubilise cytoplasmic components of cells. No previous study has applied the salt-based treatment to remove cellular components within the hAM. The present investigation analyzed the effects of the decellularization method on the cell behaviour. The stroma side of the hAM tissue was selected as the seeded site because of its greater ability to promote cell migration through the scaffold in a better way than the basement membrane (Jin et al., (2007) *Tissue Eng.* 13: 693-702).

DAPI and SMC proliferation data have shown that both decellularization types are efficient at removing whole cells yet allow recellularization of the scaffold. These results support both SDS and salt decellularization methods as options for treating the hAM. Cells were able to proliferate within the hAM scaffold as both flat and tubular constructs under these in vitro conditions, confirming the ability of cells to develop on both basement and stroma surfaces of the hAM. Flat single membrane SDS-treated hAM displayed a higher DNA concentration, on rolled constructs, an increased cell proliferation was found for salt decellularized hAM. Metabolic activity measured on flat constructs decreased in parallel with an increased cell proliferation for both types of decellularized hAM. Thus, after an initial lag phase due to the cell adaptation to its environment, they tend to develop a "normal" metabolic activity profile within the scaffold.

On rolled constructs, SMC's metabolic activity on salt-treated hAM decreased while cell proliferation increased. At the same time point, SDS-treated rolled hAM displayed a different profile. Although cell proliferation remained constant, the cell metabolic activity increased. Thus, for vessel engineering perspectives, salt-treated hAM provided beneficial results for cell proliferation.

Similarly GAG secretion on flat constructs was higher on SDS constructs at day 10, attaining a final GAG content at day 40 similar to salt-treated hAM. On rolled hAM, salt-treated hAM revealed a significantly higher content in GAGs, suggesting a greater ability of SMCs to secret non-structural extracellular matrix. These results evoke a better ability of smooth muscle cells to invade the multilayered scaffolds decellularized with salt (less aggressive for the ECM and with a lower molecular weight than SDS, thus easier to remove during the washing steps of the decellularization process).

The modulus values of flat hAM at the breaking point were not significantly different between the salt decellularized tissue and SDS-treated tissue. However, the rolled hAM displayed a significantly lower elastic modulus at breaking point from day 30 to day 40, indicating that salt-treated hAM lead to a proliferative profile of SMCs and SDS-treated hAM induces a contractile profile of SMCs (making the constructs stiffer).

The analysis of the physiological range Young modulus is relevant for TEBVs construction because the material once implanted in a host body would be extended by the blood flow and is less likely to be subject at forces as high as 30 Mpa. Thus, in the physiologic range, Young modulus curves of salt and SDS rolled treated hAM have the same trend, but SDS-treated hAM Young's modulus were double as salt-treated hAM. In physiological stresses, SDS decellularized constructs would be stiffer than salt-treated hAM.

A link between the decellularization method and cell behaviour exists; different decellularization approaches may promote specific cellular phenotypes directed toward either proliferation or a more differentiated "contractile" state. Confirming this hypothesis, the results of the present disclosure show that cells disposed on salt-treated hAM adopt a proliferative profile whereas SMCs seeded on SDS-treated hAM adopt a contractile profile. RT-PCR analysis aimed to quantify difference in gene expression on cells culture on scaffolds treated with either decellularization processes. The aim was to determine if any specific phenotype tendency may occur as a function of the scaffold chemical decellularization treatment.

The α-actin gene encodes for a protein, with its isoforms identified as being a major constituent of the contractile apparatus, which is expressed in the early stages of SMCs differentiation. Similarly, the SM22 gene encodes for a protein that enhance the SMCs contractility and mobility (Han et al., (2009) Life Sci. 84: .394-401). The specific phenotypic markers α-actin and SM22 are expressed in higher levels when SMCs adopt a contractile phenotype. The results show that scaffolds decellularized with SDS displayed a significantly higher expression of α-actin than the salt-treated samples. As well as in adult blood vessels, the seeded SMCs on SDS displayed a low rate of proliferation/turnover and show a very low rate of synthesis of extracellular matrix components. Picogreen assay results suggested a stable cell viability, indicating that these cells are virtually committed to carrying out their contractile function (Owens et al., (2004) Physiol. Rev. 84: 767-801). A correlation of the metabolic activity data to the cell content data support that cells within SDS-treated samples have adopted a contractile phenotype at 40 days of cell culture, whereas SMCs within salt-treated hAM have adopted a proliferative mode.

Matrix metalloproteinases (MMPs) such as MMP-2 and -9 have been established as important for smooth muscle cells (SMCs) migration into the intimal layer of blood vessels (Sindermann, et al. (2008) Cardiovasc. Pathol. 17: 72-80). Whereas MMP-9 is expressed in the initial stage of the SMC migration, MMP-2 activity is observed at a later stage after injury. In non-diseased human and experimental animal arteries, MMP-2 (72-kDa gelatinase) and TIMP-2 are constitutively expressed at levels providing a stable balance between endogenous matrix production and matrix degradation. The data of the disclosure shows only an up-regulation of MMP-2, and the balance between production of matrix-degrading MMPs and tissue inhibitor of metalloproteinase (TIMPs) is in favor of general matrix degradation. Corroborating these results, histological analysis show cells to have migrated into the scaffold by day 10 for the SDS-treated hAM. At day 30, a significantly higher level of MMP-2 is observed within SDS-treated rhAM as well as progressive cell migration within the scaffold as shown by histology images. Salt-treated rolled human amniotic membrane (rhAM) displayed a high level of MMP-2 at day 20, in line with the cell migration observed in the histology images, the level of expression of MMP-2 are significantly high. MMP-2 plays a more dominant role than MMP-9 in these early stage degradation events. Using collagen type II (COL2A1) and elastin as markers for extracellular matrix synthesis, collagen type II is shown to be up-regulated in cells within scaffolds decellularized with either method at days 10 and 20. No expression was detected for elastin at any time points.

Results show that SDS decellularized flat hAM displays improved SMCs growth and higher sulphated sugar content. The flat hAM salt decellularized scaffolds were more elastic and presented higher metabolic activity/cell. Conversely, rolled hAM treated with salt displayed improved SMC growth and function, higher GAGs content values as well as increased elastic properties.

Thus host cells may regenerate fully functional vascular tissues under dynamic conditions using the salt decellularization conditions. These initial results show that the hAM scaffold is promising for the in vitro construction of a blood vessel.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Procurement and isolation of the hAM: Full-term human placentas (stored at 4° C.) were collected and processed the morning of collection. hAM samples were manually peeled from the chorionic membrane and rinsed two times in distilled water, leaving approximately 2 cm of tissue around the umbilical cord. This was done to maintain tissue homogeneity as the membrane thickens substantially in this region.

Example 2

Figure 11:
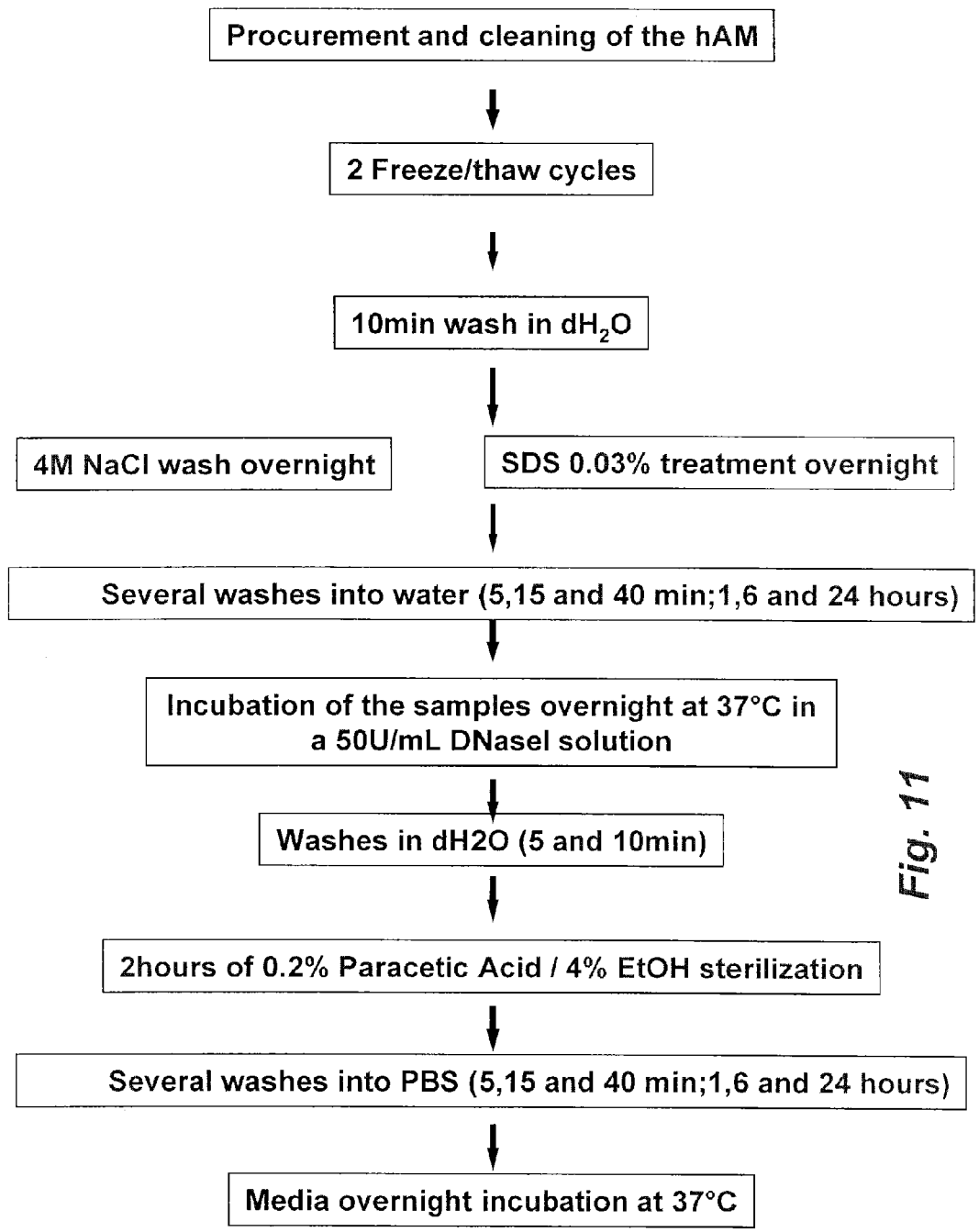
FIG. 11 schematically presents a flowchart for the preparation of the amniotic tissues according to the present disclosure.

Scaffold preparation: Methods of scaffold preparation are schematically shown in FIG. 11. After hAM harvest, cells were devitalized by 2 cycles of freezing (2 hours at −86° C.) and thawing. (15 min at 37° C.). Samples were divided into 2 sets and immersed in the appropriate decellularization solution: 0.03% (w/v) SDS or 4M NaCl and agitated at 100 rpm on a horizontal shaker plate for 24 h at 25° C.

Samples were then rinsed with fresh solutions under the same conditions in distilled water at 5, 15, 40 minutes, 1 hour, 6 hours and 24 hours. hAM's were then incubated overnight at 37° C. in 50 U/mL Desoxyribonuclease (DNase) solution (Sigma, St. Louis, Mo., USA). After a 10 min rinse in distilled water, hAM were sterilized 2 hours via a 0.01% (vol/vol) peracetic and Ethanol (2% vol/vol) solution (Fluka, Switzerland), and rinsed in PBS as above to remove residual eventual peracetic acid residues. Resulting decellularized hAM were cut into 15 mm in diameter disks to assess the flat membrane, and into 12.4×8.4 $cm^2$ rectangular shapes for rolled scaffold experiments. Before proceeding to cell seeding, hAM constructs were incubated at 37° C. overnight in complete media.

Example 3

Cell culture and seeding protocol: Human smooth muscle cells purchased from ATCC (batch 2654), were first expanded into a monolayer and then cultured until passage 9. Cells were maintained in Dulbecco's Modified Eagle's Medium (DMEM, Gibco Life Technologies, Grand Island, N.Y., USA), supplemented with 1% penicillin-streptomycin (Gibco Life technologies, Grand Island, N.Y.), and 10% of fetal serum complex (FetalPlex, Genimini Bio-Products, West Sacramento, Calif.). Cells were cultured in a 5% $CO_2$ humidified incubator at 37° C. Media was replenished every 3 days. Subconfluent cells were enzymatically detached from the culture flasks using Trypsin (Oregon, USA Invitrogen). The stroma side, thick and soft compared to the basement membrane, had been chosen as the seeded side. Thus, under sterile conditions, 12.4×8.4 $cm^2$ rectangular hAM sections and 7.08 $cm^2$ disks were seeded onto the stromal surface with SMCs at subconfluent density (600 cells/$mm^2$). Ten days after recellularization, the rectangular hAM sections were rolled with the basement membrane directed toward the inner surface of the mandrel.

Example 4

Seeding procedure: SMCs were seeded at a subconfluent density concentration of about 600 cells/$mm^2$ on the basement membrane side of the hAM.

Example 5

DAPI analysis: At the end of each time interval, tissue sections were stained with 4'-6-diamidino-2-phenylindole (DAPI stain, Invitrogen, Oreg., USA) at a 300 nM concentration to identify cell nuclei. A Nikon E800 Epifluorescent microscope was calibrated to image 400 μm×325 μm (0.13 $cm^2$), using the 20× objective. Five random sites were selected from each sample to localize and quantify cell adhesion on hAM surface.

Figure 2:
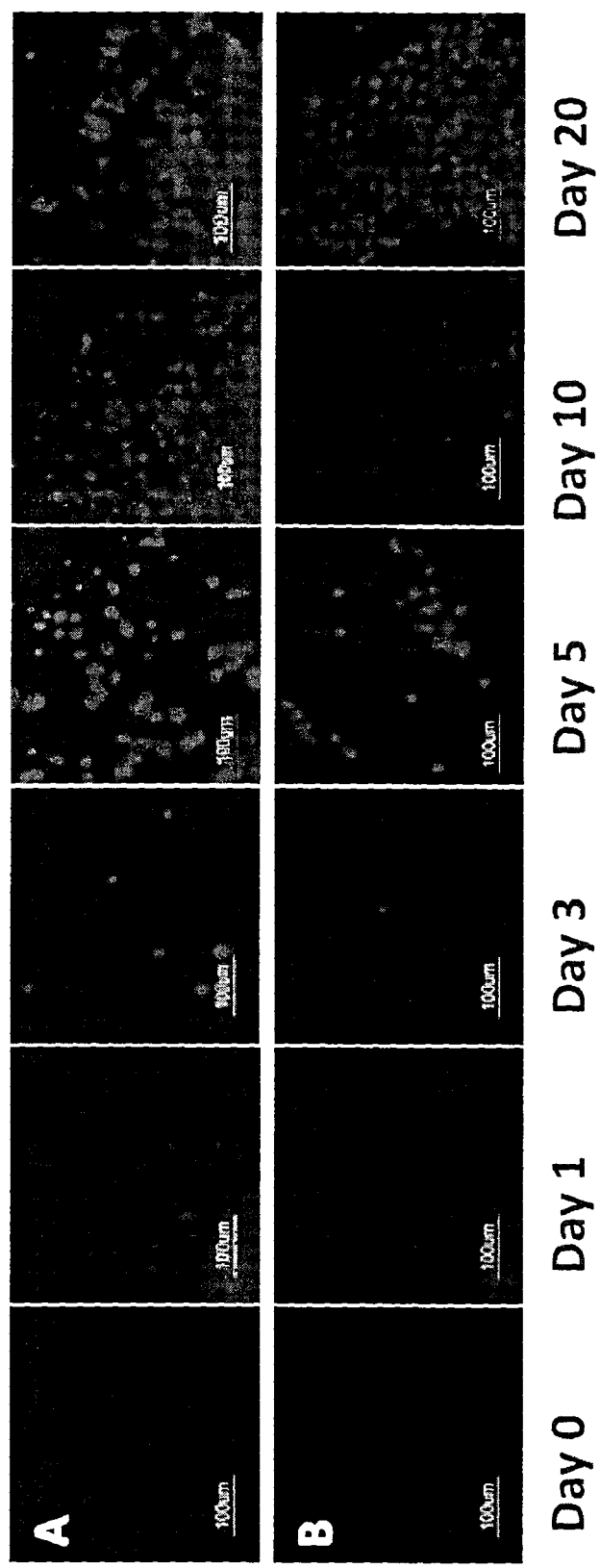
FIG. 2 shows two series of digital images showing the cell density on the hAM surface. hAM were observed under the microscope as flat sheets for both SDS (Series A) and (Series B) salt decellularization. Images show the SMCs adhered to the hAM over 20 days.

Control (devitalized samples), without seeded cells, displayed no evidence of the fluorescent dye DAPI binding, confirming both decellularization methods were efficient at removing cell nuclei on and within the hAM (FIG. 2). Seeded constructs show a qualitative increase of cell density over time with both SDS and salt decellularized hAM scaffolds.

Example 6

DNA quantification: At each time point the flat and rolled hAM section were digested using the proteolytic enzyme Papain for the digestion method (125 μg/mL) in PBS for 24 h at 60° C. to degrade the hAM. Samples were then centrifuged at 350 g for 5 min and the supernatant was analyzed using the Quanti-iT PicoGreen assay as per manufactures instructions (Invitrogen, Oreg., USA).

The DNA analysis assay showed a significant increase in DNA content over the 30 day culture period for the flat hAM. The SMCs continued to proliferate and invaded the hAM on the rolled scaffold over 40 days of cell culture. Improved proliferation is shown with the salt decellularized rhAM compared to SDS decellularized scaffolds.

Example 7

Metabolic activity: The metabolic activity of the SMCs was assessed using the Alamar Blue kit assay(Invitrogen, Oreg., USA). Absorbance was measured at 570 nm and 600 nm. The calculated reduction of Alamar Blue was used as an indicator of cell proliferation on the scaffold and correlated with a calibration curve of the same cell line, which indicates the cell health using the natural reduction of the resazurin in a red-fluorescent molecule. The fluorescence amount is proportional to the number of living cells.

Figure 13:
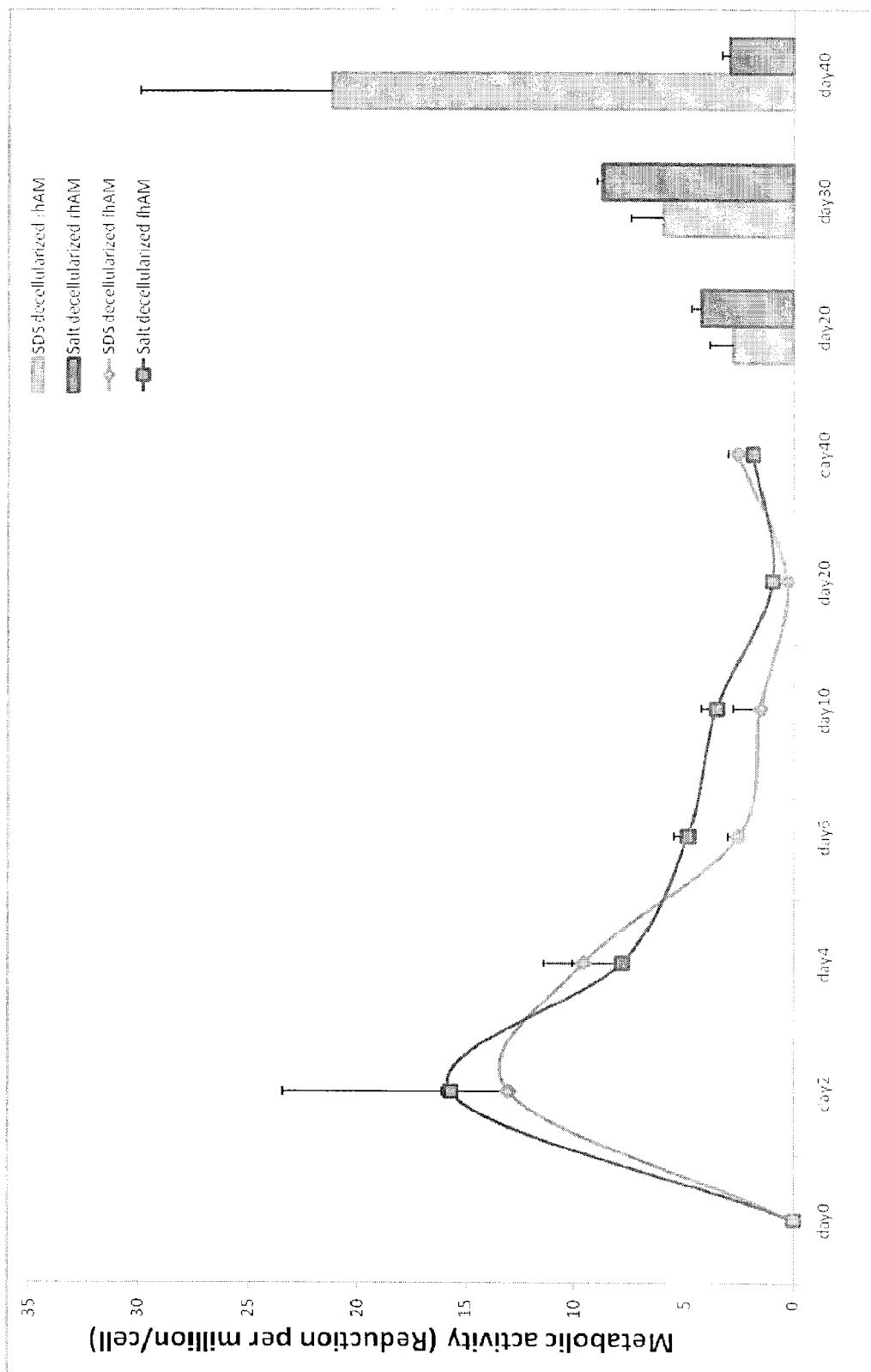
FIG. 13 shows a graph illustrating the metabolic activity of SMCs seeded on hAM. (n=9)*p<0.001.

A significant reduction in cellular metabolic activity was noted with the fhAM as cell density increased over 30 days, as shown in FIG. 13. However, the rolled hAM results show a significant increase in metabolic activity with cells seeded on both SDS and salt decellularized scaffold, with the exception of day 40, where metabolic activity significantly decreases with salt decellularized tissues.

Example 8

GAGs: Glycosaminoglycans (GAGs) quantification was assessed using the dimethylmethylene blue assay at a concentration of 46 μM in a 40 mM glycine and NaCl buffer solution (pH 3). Samples were digested in a solution containing 125 μg/mL of papain for 24 h at 60° C. The assay was calibrated using a chondroitin sulfate standard curve (Hoemann et al., (2002) *Anal. Biochem.* 300: 1-10; Farndale et al., (1986) *Biochim. Biophys. Acta.* 883: 173-177.

Figures 4A, 4B:
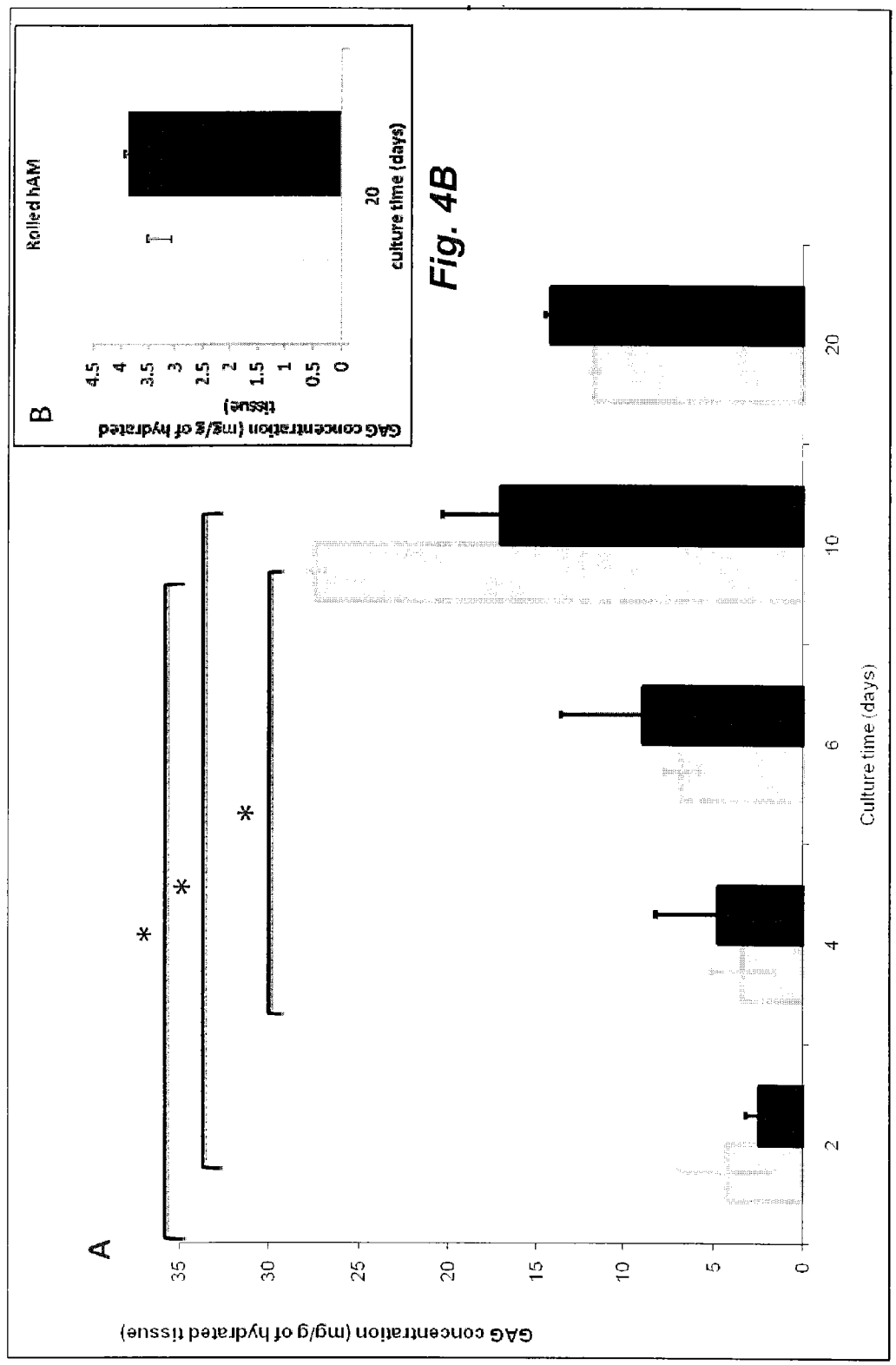
FIGS. 4A and 4B are a pair of graphs illustrating the changes in glycosaminoglycan concentration within cells seeded on SDS and salt-treated flat (FIG. 4A) and rolled (FIG. 4B) hAM (n=9).
Figure 14:
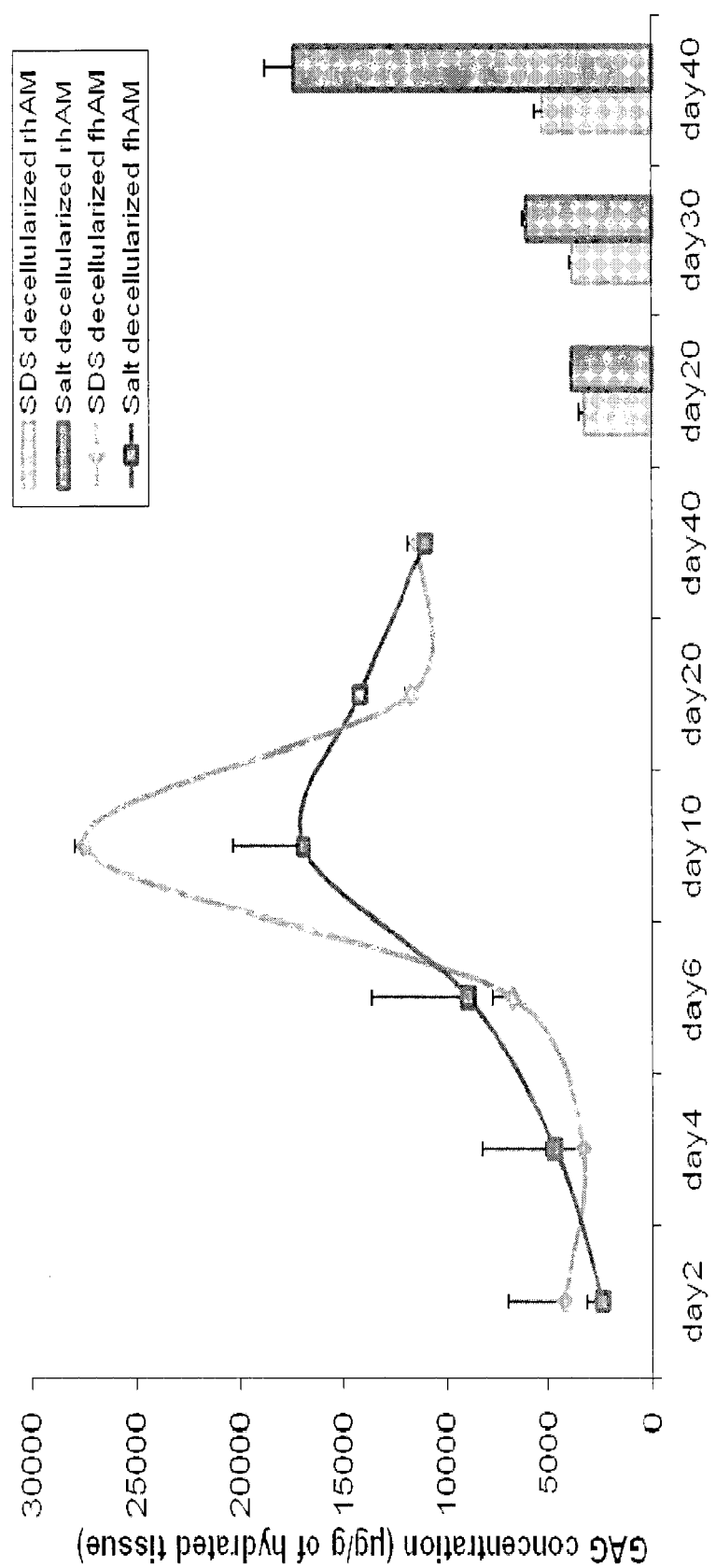
FIG. 14 shows a graph illustrating glycosaminoglycans concentration on hAM.(n=3)*p<0.001.
Figure 15:
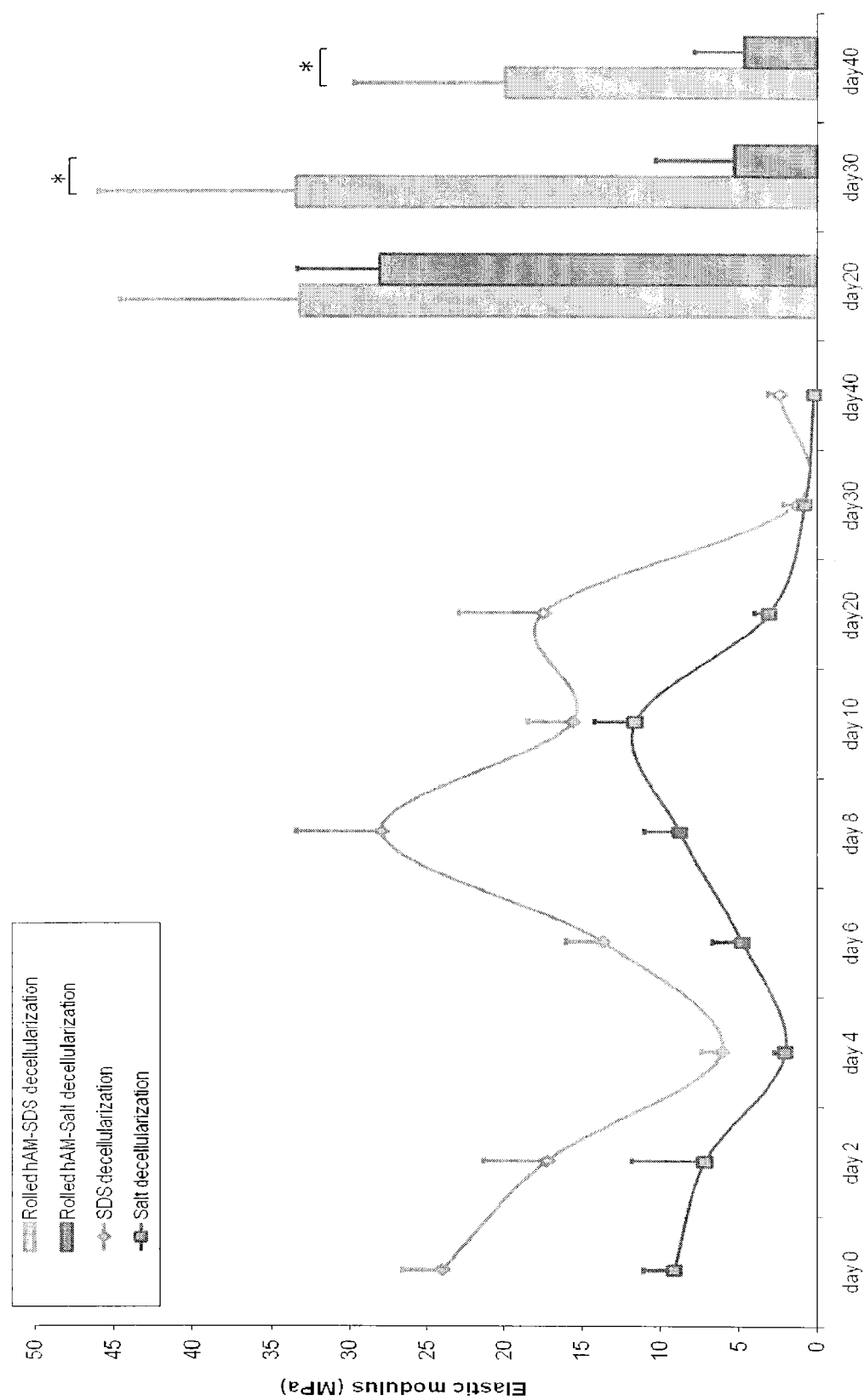
FIG. 15 shows a graph illustrating the elastic modulus of the flat.(n=5)*p<0.001.

GAGs content was shown to vary overtime dependant on the decellularization method used. Total GAGs concentration on seeded fhAM increased significantly over time in both SDS and salt decellularized scaffolds with the SDS-treated scaffold displaying enhanced GAGs concentrations peaking at day 10 (FIGS. 4A, 4B, and 14). Reaching the maximum GAGs concentration at day 10, both decellularized types of constructs displayed a reduced GAG content at day 20 and no significant difference in GAG content was observed for both decellularization at day 40 (salt and SDS constructs having approximately 11 mg of GAGs per g of hydrated tissue).

Example 9

Tissue biomechanics: Tensile properties were assessed using and Instron uniaxial testing rig (Model 5542 with Version 2.14 software; Instron, Duebendorf, Switzerland). Tissue disks were rinsed in PBS and cut to an oblong shape maintaining a 5:1 (length:width) ratio. Tissue strips were then loaded between two vertically parallel clamps. Using a constant speed of 5 mm/min samples where stretched until failure. Load and displacements values were recorded to calculate the stress/strain relationship. Stress values were calculated by dividing load to initial cross-sectional area values of each sample, using a thickness of 50 µm (Liotta et al., (1980) *Cancer Lett.* 11: 141-152; Kesting et al., (2008) *J. Burn. Care Res.* 29: 907-916; Chua & Oyen (2009) *Eur. J. Obstet. Gynecol. Reprod. Biol.* 144: S128-133). Strain values were obtained by normalizing deformation of the sample to their initial length. Using the same testing parameters rolled hAM's were cut into 5 mm wide ringlets and attached to the test rig using two stainless L-shaped hooks instead of clamps.

Example 10

SEM: Samples were fixed in gluteraldehyde 2.5% (Sigma, St Louis, Mo.) for 4 h and then washed in PBS three times, 5 min each. This was followed by a treatment of 1% osmonium solution for 2 h (Liotta et al., (1980) *Cancer Lett.* 11: 141-152; Hennerbichler et al., (2007) *Cell Tissue Bank* 8: 1-8). Samples were then progressively dehydrated in a graded series of ethanol then $CO_2$ critical point dried (Autosamdri-814, Tousimis, Rockville, Md.). Samples were then gold sputtered (Hummer IV) and analyzed using a JEOL LSM-880 SEM at 10 kV.

After decellularization both the stromal and basement membrane surfaces were assessed by scanning electron microscopy (SEM). Confirming DAPI analysis, with both types of decellularization processes, no cellular structures were noted on either surface of the scaffold. The basement and stroma surfaces displayed morphologically different structures and no specific orientation of the fibres prior and 10 days after recellularization Example 11

RNA extraction and quantitative RT-PCR: Total RNA was isolated from tissues using miVarna isolation kit (Ambion, Austin, Tex.). Thereafter, cDNA was synthesized from 2 µg of the total RNA using SuperScript VILO™ cDNA Synthesis Kit (Invitrogen). Primers for semi-quantitative RT-PCR were obtained from Synthetic miRNA oligonucleotides were purchased from Integrated DNA Technologies (IDT, Coralville, Iowa). Primer sequences for the human α-actin, collagen, MMP2, SM22, MMP9, TIMP2, myosin, elastin cDNA used in this study are given Table 1. RT-PCR reactions were run using a BioRad CFX96 and CFX384 Real-Time Systems with glyceraldehyde-3-phosphate dehydrogenase (GAPDH) used as an internal control. The cycle was defined at 95° C. for 10 min, followed by 40 cycles of denaturing at 95° C. for 15 sec, annealing/extension at 60° C. for 60 sec. The amount of DNA immunoprecipitated was determined using quantitative real-time PCR using Power SYBR green PCR master mix (Applied Biosystems). Relative mRNA levels were evaluated by BioRad CFX Manager Software (BioRad, USA) and expressed as the fold difference relative to GAPDH mRNA levels.

Figure 9:
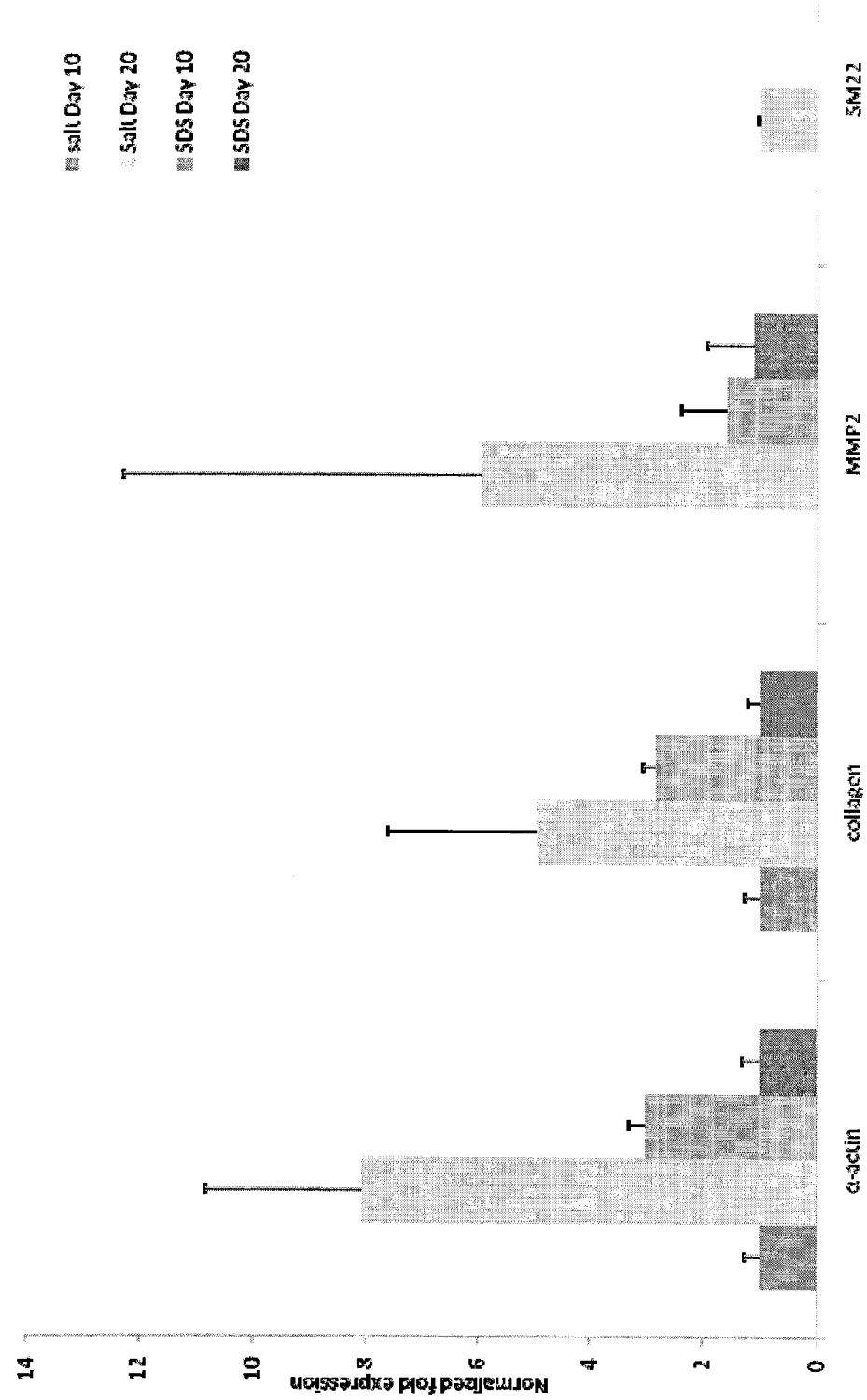
FIG. 9 shows a graph illustrating the results of RT-PCR of α-actin, collagen, MMP2 and SM22 of hAM treated with salt and SDS. Day 20 data corresponds to rolled hAM.

The expression patterns of matrix remodeling enzymes MMP-2, -9 and TIMP-2 were assessed, as well as α-actin, collagen and SM22 (FIG. 9). No expression of MMP-9 and TIMP-2 was detected in all the samples; however MMP-2 was expressed at day 20 for the rolled salt-treated samples and its expression significantly decreased at day 40. Concerning rolled SDS-treated samples, the expression pattern is different. MMP-2 is expressed from day 10 and increased significantly at day 40. The matrix remodeling gene collagen type II was expressed at day 10 and 20 for both salt and SDS-treated samples with a significant increase of secretion between day 10 and day 20 for salt-treated rhAM and a decrease of expression for SDS-treated samples. SMCs were also evaluated for the expression of cell specific phenotypic markers α-actin and SM22. Importantly, longer term cultures (up to 40 days) assessed local variation in cell behavior, in particular to determine proliferative or contractile state of SMCs. α-actin was expressed at each time point, however the pick of expression is at day 20 for salt-treated samples and at day 40 of cell seeding for the SDS-treated rhAM. Similarly, a high level of expression of the gene SM22 was noticed at day 40 of cell seeding for SDS-treated rhAM.

TABLE 1

Primers sequences for the human α-actin, collagen, MMP2, SM22, MMP9, TIMP2, myosin and elastin genes.

| Gene | Sense (5'→3') | Antisense (5'→3') |
|---|---|---|
| MMP 9 (537 bp) | CGGAGCACGGAGACGGGTAT (SEQ ID No. 1) | TGAAGGGGAAGACGCACAGC (SEQ ID No. 2) |
| MMP-2 | GTATTTGATGGCATCGCTCA (SEQ ID No. 3) | CATTCCCTGCAAAGAACACA (SEQ ID No. 4) |
| TIMP-2 | CTCGCTGGACGTTGGAGGAAAGAA (SEQ ID No. 5) | TGAACCACAGGTACCAGATGGGCT (SEQ ID No. 6) |
| Myosin heavy-chain 353 bp | forward primer TCAGCAACGAGCTGGCCACAG (SEQ ID No. 7) | reverse primer TGGCGTTGATGCGCTGGGACTC (SEQ ID No. 8) |
| SM α actin | reverse primer GGTGGGATGCTCTTCAGG (SEQ ID No. 9) | forward primer CATCACCAACTGGGACGA (SEQ ID No. 10) |
| Elastin | | |
| Collagen | Reverse TCTTGCAGTGGTAGGTGATGTTCT (SEQ ID No. 11) | Forward ATGTGGCCATCCAGCTGAC (SEQ ID No. 12) |

Example 12

Histology: Samples were cut in 5 μm sections using a cryostat and disposed on the top of slides (VWR) and then were submerged into the following protocol: rinse in deionized water for 30 sec, immersion in hematoxylin for 90 sec, in tap water for 1 min, immersed in Blue reagent 30 sec, rinse in deionized water, graded dehydration 30 sec each of 70%, 80%, 95%, and 100% ethanol, immersed into a Clear-rite solution for 30 sec twice, and then using mounting media and covered by a coverslip.

Figure 8:
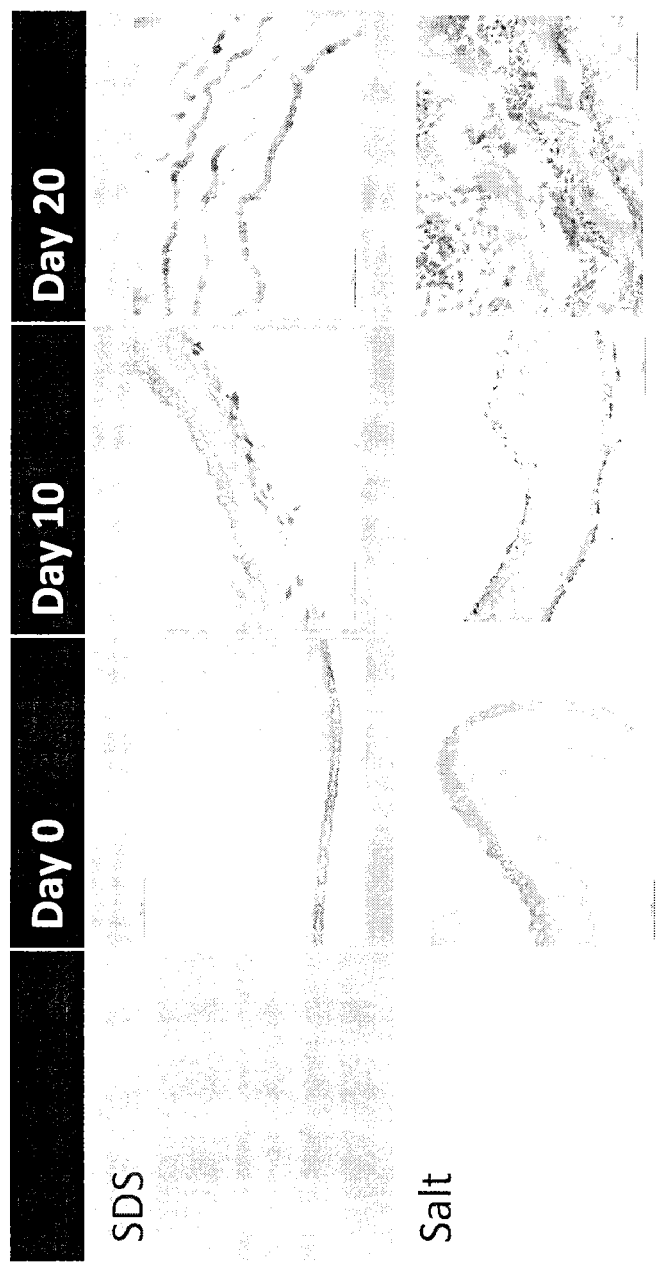
FIG. 8 shows a series of digital histological images of the flat and rolled hAM treated with salt and SDS.

In accordance with DAPI, cell proliferation results, histology images displayed an increasing cell population within time on both types of treated hAM (FIG. 8). Furthermore, a cell migration is observed as early as day 10 in both SDS and salt-treated hAM, as well on rolled than on flat constructs. At day 40, cell migration on SDS constructs is located preferentially on media/scaffold surfaces.

Example 13

Statistical analysis: Data are presented as mean values+/−standard deviation (SD) from at least three independents experiments (n=3). Statistical analysis was performed using the two-way ANOVA method with significant differences corresponding to a $p<0.01$ (confidence level $\geq 99\%$).

Example 14

Figure 12:
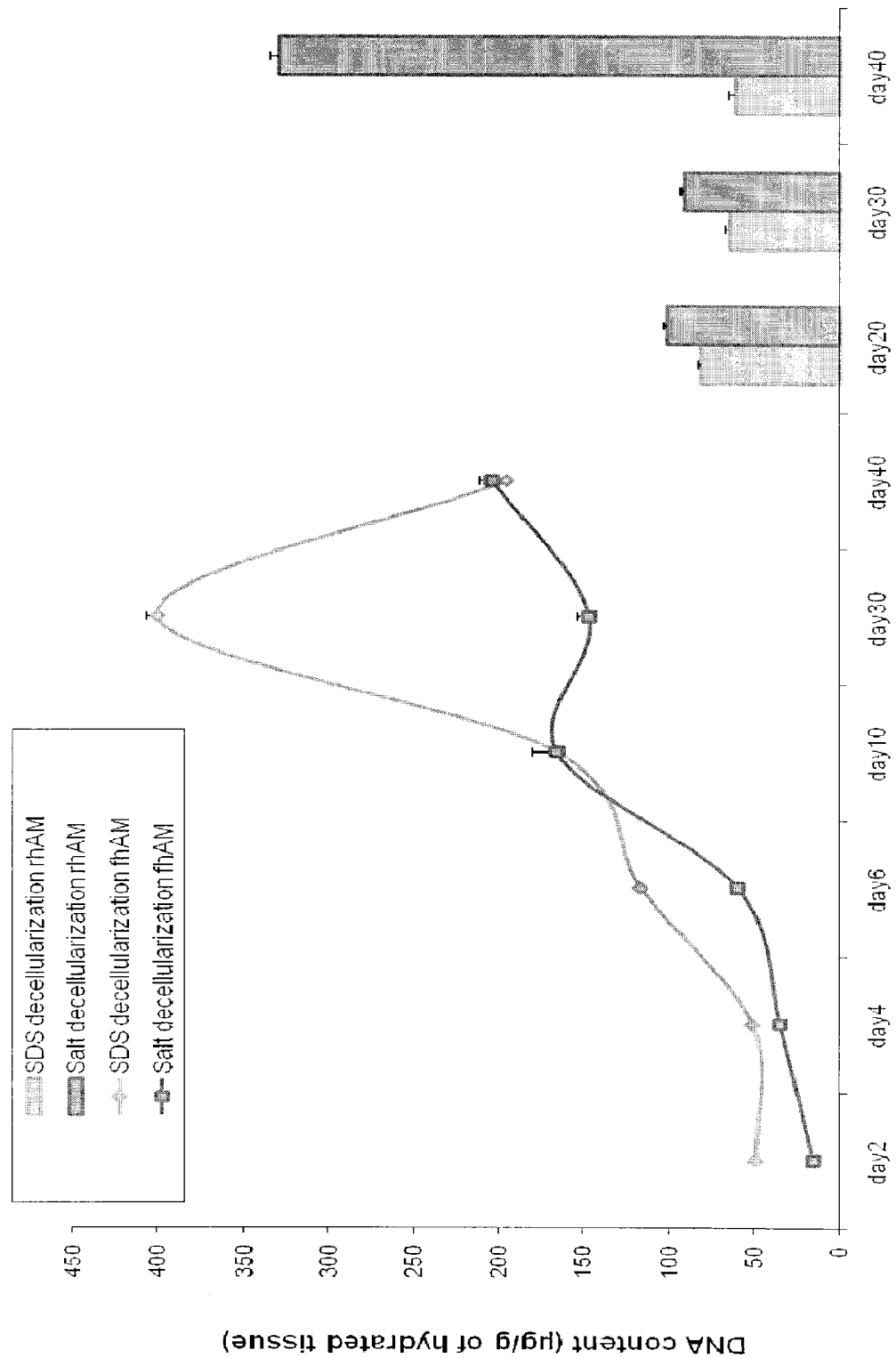
FIG. 12 shows a graph illustrating the proliferation of smooth muscle cells on hAM. (n=9)*p<0.001.

SMCs proliferation and metabolic activity: SMCs seeded on the flat hAM membrane decellularized by either method displayed a significant increase in cell density over the first 10 days of culture (FIGS. 3A and 3B). By day 30, salt-treated flat hAM displayed a 2-fold increase in DNA content compared to SDS-treated scaffolds. However, by day 40, DNA content of both decellularization types was similar, reaching approximately 200 μg of DNA/g of hydrated tissue. Although the SMCs displayed a slightly higher density on rolled human Amniotic Membrane (rhAM) treated with SDS, both treatments remained constant between days 20 and day 30. However, by day 40 salt decellularized rolled constructs displayed a 7 times increase in DNA concentration than SDS decellularized rolled scaffolds (FIGS. 3A, 3B, and 12).

A progressive decline in metabolic activity totalling 88% was noted in both SDS and salt-decellularized flat hAM scaffolds from day 2 to day 40. Results with the rolled hAM contrasted the flat scaffolds, with the metabolic activity of both SDS and salt decellularized scaffolds slowly increasing between days 20 and day 30. At day 40, the metabolic activity of SMC's on salt-treated hAM decreased as cell density increased, while cells on the SDS decellularized hAM displayed a sharply higher metabolic activity while the cell number remained stable.

Example 15

Biomechanical properties: elastic modulus at the failure point and at the physiological range: SDS decellularized scaffolds showed a higher Young modulus value compared to salt decellularized hAM for both flat and rolled constructs over time (FIGS. 5A-7B). After recellularization, Young modulus values decreased gradually with both decellularization methods until day 4. This was followed by an increase of stiffness of flat scaffolds until day 8 for SDS decellularized flat hAM and day 10 for salt decellularized hAM. After this point, both SDS and salt decellularized tissues displayed a progressive decrease in stiffness up to day 40.

Figures 5A, 5B:
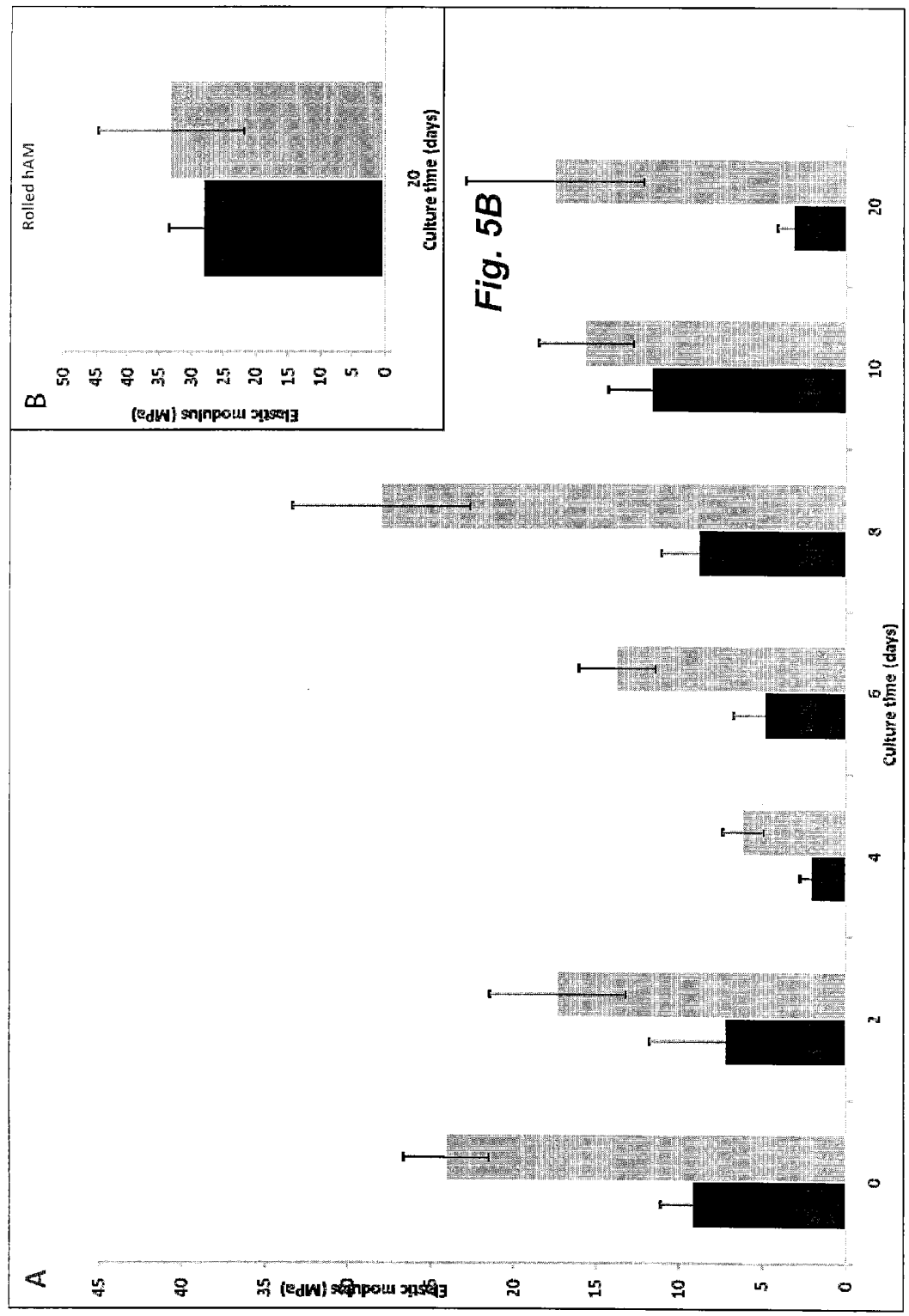
FIGS. 5A and 5B are a pair of graphs illustrating Young's modulus comparison of SDS and salt decellularized flat (5.a) and rolled (5.b) hAM (n=5).

Ten days following the rolling process, a high Young modulus (33 MPa and 28 MPa for the SDS and salt-treated respectively) was observed for the both decellularization types (FIG. 5B). While SDS-treated hAM displayed no statistical difference of Young Modulus values, salt decellularized hAM Young's modulus values dropped from 28.074 MPa until 5.28 MPa between days 20 and day 30 of cell seeding. From day 30 to day 40 of cell seeding, the rolled salt-based hAM Young modulus remained stable.

Figures 6A, 6B:
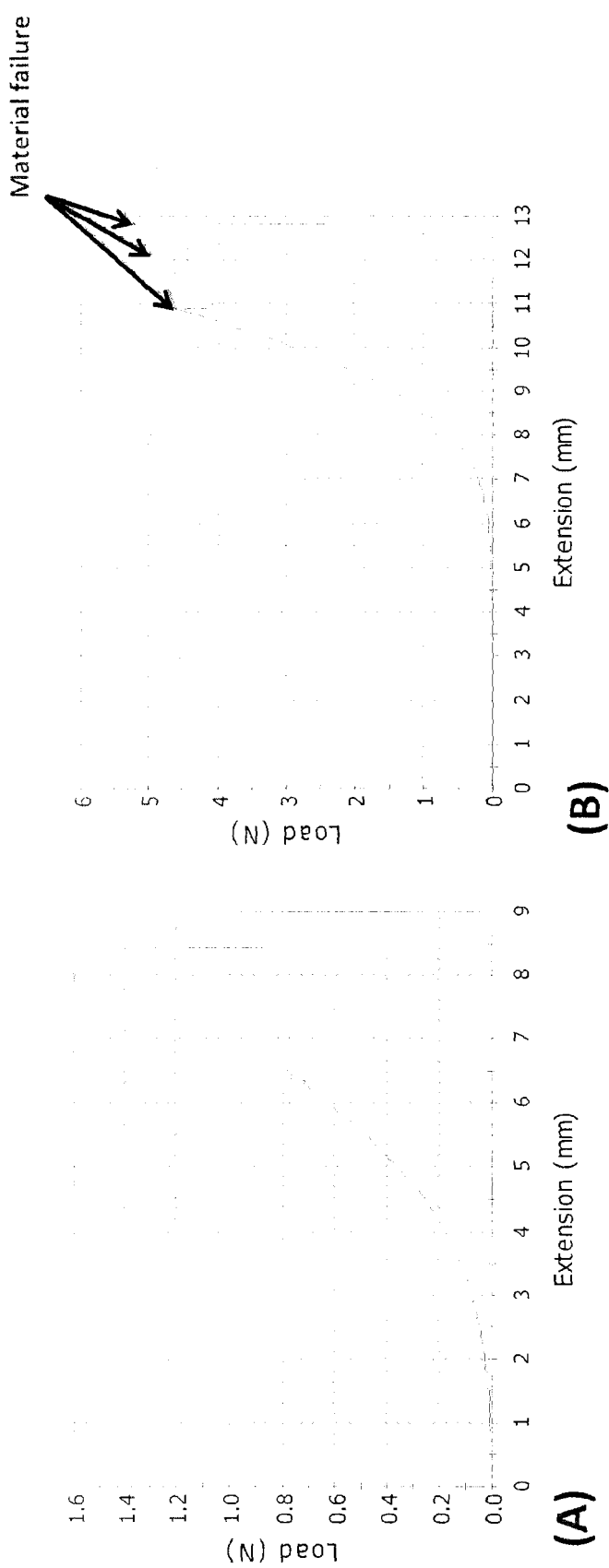
FIGS. 6A and 6B are a pair of graphs illustrating hAM failure profile during the biomechanical test. Data represent stress-strain graph for flat (FIG. 6A) and rolled (FIG. 6B) hAM constructs.
Figures 7A, 7B:
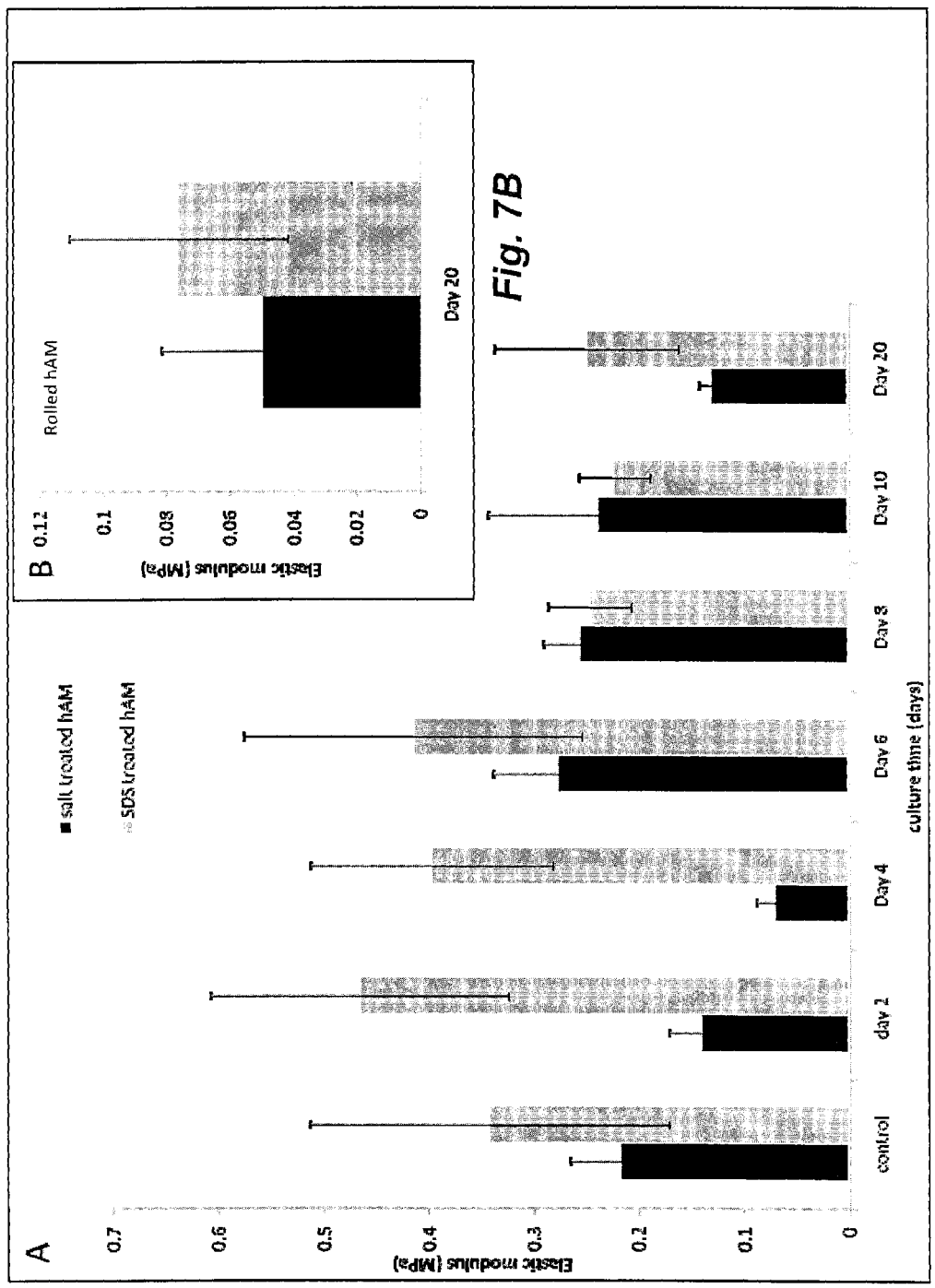
FIGS. 7A and 7B are a pair of graphs illustrating elastic modulus comparisons of SDS and salt decellularized flat (FIG. 7A) and rolled (FIG. 7B) hAM in the physiological range (n=5).

The curve profile of the rolled constructs displayed different material failure points, related to the number of layers of the rolled constructs (each single layer failure caused by the applied stress can be seen (FIG. 6A). Flat constructs displayed as well an incremental Young modulus as the exerted load increased but, presented a single breaking point (FIG. 6B).

Figures 10A, 10B:
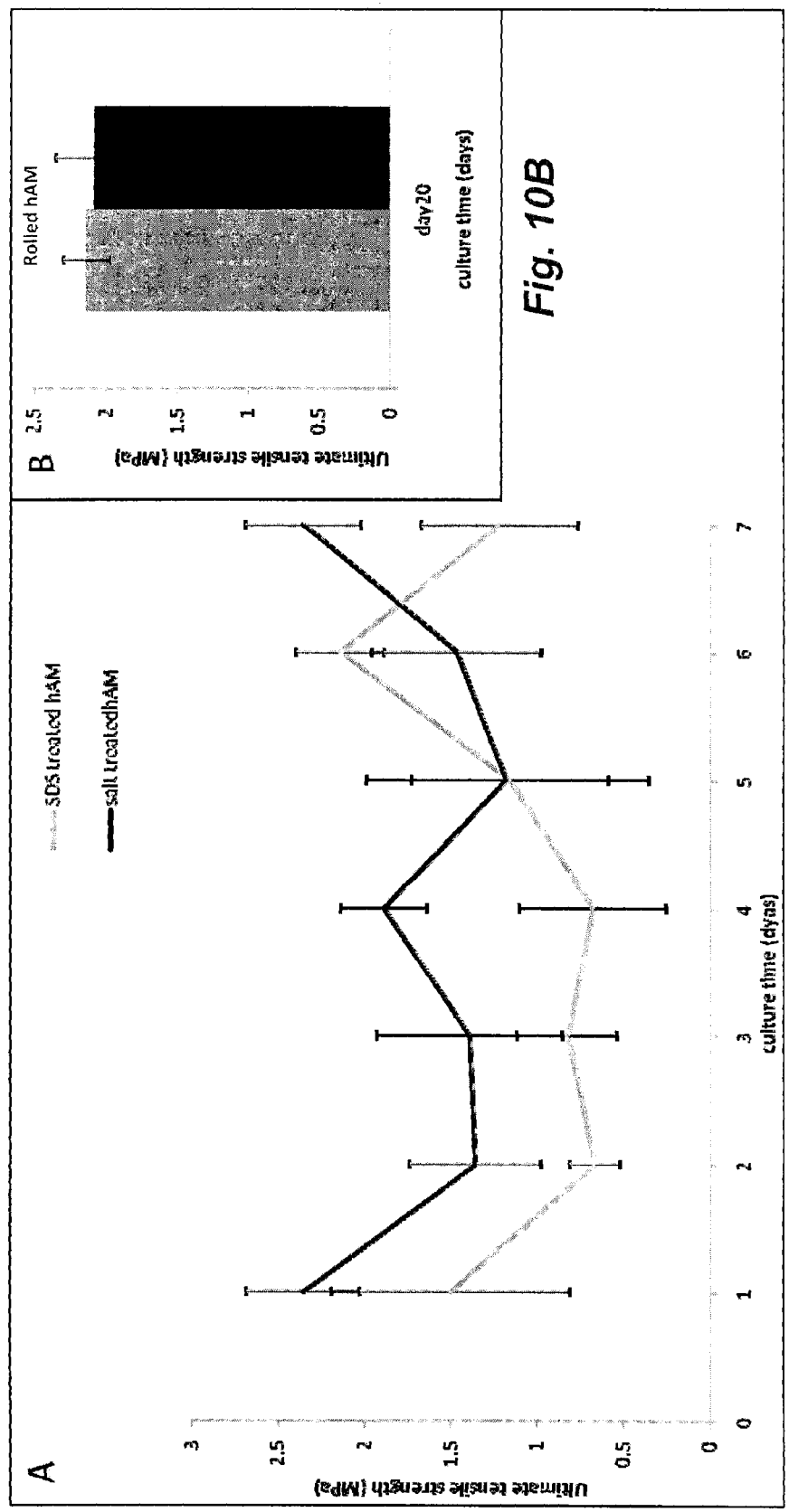
FIGS. 10A and 10B are a pair of graphs illustrating the tensile strengths of flat hAM versus rolled hAM.

Data analysis of Young modulus expressed during the physiological range, i.e. at 10% of the maximum extension reached by the constructs, are close to the human natural blood vessel values registered (FIGS. 10A and 10B). In parallel with the elastic modulus measured at the breaking point, SDS constructs on flat and rolled constructs had higher elastic modulus values than salt constructs. Rolled salt constructs elastic modulus curves displayed the same profile on the failure point than on the physiological range. However, SDS constructs on the physiological range have the same trend than salt, which is not observed at the failure point.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of the numerical value, or more of the numerical value(s) being modified.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim the following:

1. A method of forming a multi-layered implantation material, comprising the steps of:

obtaining an amniotic membrane;

decellularizing the amniotic membrane to produce a decellularized amniotic membrane;

forming a multi-layered implantation material by wrapping the amniotic membrane around itself to form a multi-layered structure having a spiral roll cross-section with two or more spiral layers;

freeze drying the multi-layered implantation material; and after forming the multi-layered implantation material, culturing the multi-layered implantation material under conditions whereby the membrane is colonized by a population of cells.

2. The method of claim 1, wherein the decellularized amniotic membrane is substantially free of non-amniotic tissue.

3. The method of claim 1, wherein the amniotic membrane is decellularized by contact with sodium dodecyl sulphate or sodium chloride.

4. The method of claim 1, wherein the amniotic membrane is decellularized by contact with sodium chloride.

5. The method of claim 1, wherein the multi-layered implantation material is an implant for a subject human or animal.

6. The method of claim 1, further comprising: disposing the multi-layered implantation material onto a second multi-layered implantation material to form a structure; and freeze drying the structure.

7. The method of claim 6, further comprising: drilling a plurality of drilled holes in the amniotic membrane.

8. The method of claim 6, wherein the drilled holes can have a diameter of about 1 to 500 micrometers and wherein one or more pairs of drilled holes are spaced by about 1 micrometer to 10 millimeters.

9. The method of claim 1, further comprising: drilling a plurality of holes in the multi-layered amniotic membrane before wrapping the amniotic membrane around itself.

10. The method of claim 9, wherein the drilled holes can have a diameter of about 1 to 500 micrometers and wherein one or more pairs of drilled holes are spaced by about 1 micrometer to 10 millimeters.

11. The method of claim 9, further comprising: freeze drying the amniotic membrane before drilling the plurality of holes.

12. The method of claim 11, further comprising: cross-linking the multi-layered amniotic membrane.

13. The method of claim 1, wherein wrapping includes wrapping the multi-layered implantation material around a structure to form the multi-layered implantation structure having the spiral roll cross-section, wherein removal of the structure provides a lumen oriented along the longitudinal axis of the multi-layered implantation structure.

14. The method of claim 13, wherein the lumen has a substantially circular cross-section.

15. The method of claim 13, wherein the lumen has a diameter of about 0.2 mm to 30 mm and wherein the multi-layered implant has a diameter of about 1 mm to 30 mm.

16. The method of claim 1, wherein the population of cells is selected from the group consisting of: a stem cell, an endothelial cell, a smooth muscle cell, a fibroblast, and a combination thereof.

17. The method of claim 1, wherein the population of cells is a homogeneous population of cells.

18. The method of claim 1, wherein the population of cells is a heterogeneous population of cells.

19. A method of forming a multi-layered implantation material having a spiral roll cross-section, comprising the steps of:
wrapping an amniotic membrane around itself to form a multi-layered structure having the spiral roll cross-section, wherein the multi-layered implant has two or more spiral layers; and
freeze drying the multi-layered structure.

20. The method of claim 19, wherein the multi-layered implantation material has an inner edge, an outer edge, and a longitudinal axis along the length of the multi-layered implant.

21. The method of claim 19, wherein the multi-layered structure has a plurality of holes.

22. The method of claim 19, further comprising: cross-linking the multi-layered structure.

23. The method of claim 19, further comprising: drilling a plurality of holes in the multi-layered structure.

24. The method of claim 19, further comprising disposing a population of cells on said amniotic membrane before wrapping.

25. The method of claim 24, further comprising decellularizing the amniotic membrane before disposing the population of cells on the amniotic membrane.

26. The method of claim 24, wherein the lumen has a diameter of about 0.2 mm to 30 mm and wherein the multi-layered implant has a outside diameter of about 1 mm to 30 mm.

27. The method of claim 19, further comprising decellularizing the amniotic membrane before wrapping.

28. The method of claim 19, wherein each spiral layer has a thickness of about 45 µm to 2000 µm.

29. The method of claim 19, wherein the multi-layered implantation material has a width along the longitudinal axis of about 0.01 mm to 1200 mm.

30. A method of forming a non-synthetic, multi-layered implantation tubular scaffold, the method comprising:
wrapping an amniotic membrane around itself to form a multi-layered implantation tubular scaffold having a spiral roll cross-section with two or more spiral layers;
optionally freeze drying the multi-layered implantation tubular scaffold; and
optionally culturing the multi-layered implantation tubular scaffold under conditions whereby the membrane is colonized by a populations of cells;
wherein the multi-layered implantation tubular scaffold does not comprise synthetic materials.

* * * * *

UNITED STATES PATENT AND TRADEMARK OFFICE
CERTIFICATE OF CORRECTION

PATENT NO. : 9,433,490 B2
APPLICATION NO. : 13/994915
DATED : September 6, 2016
INVENTOR(S) : Peter McFetridge It is certified that error appears in the above-identified patent and that said Letters Patent is hereby corrected as shown below:

Column 1 Line 22 change "NIH Grant No. R01 1050916 awarded by the U.S. National" to "NIH Grant No. R01 HL088207 awarded by the U.S. National"

Signed and Sealed this
Seventh Day of March, 2017

Michelle K. Lee
*Director of the United States Patent and Trademark Office*